(12) United States Patent
Yan et al.

(10) Patent No.: US 11,525,005 B2
(45) Date of Patent: Dec. 13, 2022

(54) ANTI-CD40 ANTIBODY, ANTIGEN BINDING FRAGMENT THEREOF AND MEDICAL USE THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Shude Yan, Lianyungang (CN); Jiahua Jiang, Lianyungang (CN); Qiyue Hu, Shanghai (CN); Lianshan Zhang, Lianyungang (CN); Guoqing Cao, Lianyungang (CN); Xueming Qian, Suzhou (CN); Fei Teng, Suzhou (CN)

(73) Assignees: Jiangsu Hengrui Medicine Co., Ltd., Lianyungang (CN); Shanghai Hengrui Pharmaceutical Co., Ltd., Shanghai (CN)

(*) Notice: Subject to any disclaimer, the term of this patent is extended or adjusted under 35 U.S.C. 154(b) by 69 days.

(21) Appl. No.: 16/618,006

(22) PCT Filed: May 31, 2018

(86) PCT No.: PCT/CN2018/089252
§ 371 (c)(1),
(2) Date: Nov. 27, 2019

(87) PCT Pub. No.: WO2018/219327
PCT Pub. Date: Dec. 6, 2018

(65) Prior Publication Data
US 2020/0148778 A1 May 14, 2020

(30) Foreign Application Priority Data
Jun. 1, 2017 (CN) .......................... 201710402559.0

(51) Int. Cl.
C07K 16/28 (2006.01)
C07K 16/30 (2006.01)
A61K 39/00 (2006.01)
A61K 38/00 (2006.01)
C12N 5/12 (2006.01)

(52) U.S. Cl.
CPC .......... C07K 16/2875 (2013.01); *A61K 38/00* (2013.01); *A61K 39/00* (2013.01); *C07K 2317/565* (2013.01); *C12N 5/12* (2013.01)

(58) Field of Classification Search
None
See application file for complete search history.

(56) References Cited

U.S. PATENT DOCUMENTS 9,334,331 B2 * 5/2016 Igawa ................... C07K 16/36
10,421,807 B2 * 9/2019 Gonzales ................ A61P 17/08
2008/0254026 A1 * 10/2008 Long ..................... A61K 39/395
424/133.1
2014/0349395 A1 * 11/2014 Zhang ..................... A61P 35/00
435/328
2017/0015754 A1 1/2017 Suri et al.

FOREIGN PATENT DOCUMENTS

| CN | 1198647 | 11/1998 |
|---|---|---|
| CN | 101237882 | 8/2000 |
| CN | 1369015 | 9/2002 |
| CN | 1522264 | 8/2004 |
| CN | 1582165 | 2/2005 |
| CN | 101014386 | 8/2007 |
| CN | 101289510 | 10/2008 |
| CN | 100430419 | 11/2008 |
| CN | 101490086 | 7/2009 |
| CN | 101508734 | 8/2009 |
| CN | 102448989 | 5/2012 |
| CN | 102918063 | 2/2013 |
| CN | 103842382 | 6/2014 |
| CN | 104918957 | 9/2015 |
| TW | 200306204 | 11/2003 |
| WO | WO 2002028904 | 4/2002 |
| WO | WO 2011123489 | 10/2011 |
| WO | WO 2012149356 | 11/2012 |
| WO | WO 2013034904 | 3/2013 |
| WO | WO 2015091853 | 6/2015 |
| WO | WO 2016/168149 | 10/2016 |
| WO | WO 2016196314 | 12/2016 |
| WO | WO 2017004006 | 1/2017 |

(Continued)

OTHER PUBLICATIONS

Leong et al. Preparing recombinant single chain antibodies. Chemical Engineering Science 63:1401-1414 (2008). (Year: 2008).*
Leath et al. Single chain antibodies: A therapeutic modality for cancer gene therapy Review, International Journal of Oncology, vol. 24:765-771, (2004). (Year: 2004).*
Al Qaraghuli et al. Antibody-protein binding and conformational changes: identifying allosteric signaling pathways to engineer a better effector response. Nature Scientific Reports 10:13969; (2020). (Year: 2020).*
Tokuriki et al. Stability effects of mutations and protein evolvability, Current Opinion in Structural Biology, 19:596-604, (2009). (Year: 2009).*

(Continued)

Primary Examiner — Elizabeth C. Kemmerer
Assistant Examiner — Regina M DeBerry
(74) Attorney, Agent, or Firm — Fish & Richardson P.C.

(57) ABSTRACT

Provided are an anti-CD40 antibody, an antigen binding fragment thereof, and a medical use thereof. Also provided are a chimeric antibody and a humanized antibody including a CDR region of the anti-CD40 antibody, a pharmaceutical composition including the human anti-CD40 antibody and the antigen binding fragment thereof, and an application thereof as an anti-cancer drug. In particular, provided are a humanized anti-CD40 antibody, and an application thereof in preparation of a drug to treat a CD40-mediated disease or disorder.

25 Claims, 2 Drawing Sheets
Specification includes a Sequence Listing.

(56) References Cited

FOREIGN PATENT DOCUMENTS

| WO | WO 2017040932 | 3/2017 |
|---|---|---|
| WO | WO 2017/121307 | 7/2017 |

OTHER PUBLICATIONS

Bhattacharya et al. Impact of genetic variation on three dimensional structure and function of proteins; PLOS One 12(3): e0171355, pp. 1-22, (Mar. 2017). (Year: 2017).*

Edwards et al. The remarkable flexibility of the human antibody repertoire; isolation of over one thousand different antibodies to a single protein, BLyS. Journal of Molecular Biology 334:103-118; (2003). (Year: 2003).*

Lloyd et al. Modelling the human immune response: performance of a 10(11) human antibody repertoire against a broad panel of therapeutically relevant antigens. Protein Engineering, Eng. Design & Selection 22(3): 159-168; (2009) (Year: 2009).*

Goel et al. Plasticity within the antigen-combining site may manifest as molecular mimicry in the humoral immune response. J. Immunol. 173: 7358-7367; (2004) (Year: 2004).*

Khan et al. Adjustable locks and flexible keys: plasticity of epitope-paratope interactions in germline antibodies. J. Immunol. 192: 5398-5405; (2014). (Year: 2014).*

Poosarla et al. Computational De Novo Design of Antibodies Binding to a Peptide With High Affinity. Biotechn. Bioeng. 114(6): 1331-1342; (2017). (Year: 2017).*

Rabia, et al. Understanding and overcoming trade-offs between antibody affinity, specificity, stability and solubility. Biochemical Engineering Journal 137:365-374; (2018). (Year: 2018).*

Karpova et al. Raji revisited: cytogenetics of the original Burkitt's lymphoma cell line. Leukemia 19:159-161 (2005). (Year: 2005).*

Justice et al. Using the mouse to model human disease: increasing validity and reproducibility, Disease, Models & Mechanisms 9: 101-103 (2016) (Year: 2016).*

Bajor et al., "Immune Activation and a 9-Year Ongoing Complete Remission Following CD40 Antibody Therapy and Metastasectomy in a Patient with Metastatic Melanoma," Cancer Immunology Research, 2014, 2(11):1051-1058.

Caldas et al., "Humanization of the anti-CD18 antibody 6.7: an unexpected effect of a framework residue in binding to antigen." Molecular Immunology, 2003, 39:941-952.

Du et al., "Molecular Basis of Recognition of Human Osteopontin by 23C3. a Potential Therapeutic Antibody for Treatment of Rheumatoid Arthritis," J. Mol. Biol., 2008, 382:835-842.

Panka et al., "Variable region framework differences result in decreased or increased affinity of variant anti-digoxin antibodies," 1988, 85:3080-3084.

Xiang et al., "Modification in Framework Region I Results in a Decreased Affinity of Chimeric Anti-Tag72 Antibody." Molecular Immunology, 1991, 28(1/2):141-148.

Gladue et al., "The CD40 agonist antibody CP-870,893 enhances dendritic cell and B-cell activity and promotes anti-tumor efficacy in SCID-hu mice", Cancer Immunol Immunother, vol. 60 (7), pp. 1009-1017, 2011.

Holliger et al., "Engineered Antibody Fragments and the Rise of Single Domains", Nat. Biotechnol. 23: 1126-1136, 2005.

International Search Report in International Application No. PCT/CN2018/089252, dated Sep. 5, 2018, 9 pages, English Translation.

Taiwan Office Action issued in Taiwan Patent Application No. 107118861, dated Sep. 17, 2019, 6 pages.

Tong et al., "Prospects for CD40-directed experimental therapy of human cancer",Cancer Gene Therapy, vol. 10, pp. 1-13, 2003.

Van Mierlo et al., "CD40 stimulation leads to effective therapy of CD40—tumors through induction of strong systemic cytotoxic T lymphocyte immunity", PNAS, vol. 99(8), pp. 5561-5566, 2002.

Written Opinion of International Searching Authority in International Application No. PCT/CN2018/089252, dated Sep. 5, 2018, 8 pages, English Translation.

Xiang et al., Modification in frame work region I results in a decreased affinity of chimeric anti-tag72 antibody, Molecular Immunol., 1991, 28:1/2:141-148.

\* cited by examiner

SEQUENCE LISTING

<160> NUMBER OF SEQ ID NOS: 60

<210> SEQ ID NO 1
<211> LENGTH: 116
<212> TYPE: PRT
<213> ORGANISM: Mus musculus

<400> SEQUENCE: 1

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ser Asp Tyr
            20                  25                  30

Leu Ile Glu Trp Ala Lys Gln Arg Pro Gly Gln Gly Leu Glu Trp Ile
        35                  40                  45

Gly Val Ile Asn Pro Gly Ser Gly Gly Ser Asn Tyr Asn Glu Lys Ile
    50                  55                  60

Lys Asp Arg Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Gly Gly Phe Thr Tyr Trp Gly Gln Gly Thr Leu Val
            100                 105                 110

Thr Val Ser Ala
        115

<210> SEQ ID NO 2
<211> LENGTH: 107
<212> TYPE: PRT
<213> ORGANISM: Mus musculus

<400> SEQUENCE: 2

Glu Ile Gln Leu Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Ile Lys Leu Leu Leu
        35                  40                  45

Asn Phe Ala Ser Arg Leu His Ser Gly Val Pro Ser Arg Phe Ser Gly
    50                  55                  60

Ser Gly Ser Gly Thr Asp Phe Phe Leu Thr Ile Ser Asn Leu Glu Gln
65                  70                  75                  80

Asp Asp Ile Ala Thr Tyr Phe Cys Gln Gln Gly Ser Thr Leu Pro Trp
                85                  90                  95

Thr Phe Gly Gly Gly Thr Lys Leu Glu Ile Lys
            100                 105

<210> SEQ ID NO 3
<211> LENGTH: 10
<212> TYPE: PRT
<213> ORGANISM: Mus musculus

<400> SEQUENCE: 3

-continued

Gly Tyr Ala Phe Ser Asp Tyr Leu Ile Glu
1               5                   10

<210> SEQ ID NO 4
<211> LENGTH: 17
<212> TYPE: PRT
<213> ORGANISM: Mus musculus

<400> SEQUENCE: 4

Val Ile Asn Pro Gly Ser Gly Gly Ser Asn Tyr Asn Glu Lys Ile Lys
1               5                   10                  15
Asp

<210> SEQ ID NO 5
<211> LENGTH: 7
<212> TYPE: PRT
<213> ORGANISM: Mus musculus

<400> SEQUENCE: 5

Gly Gly Gly Gly Phe Thr Tyr
1               5

<210> SEQ ID NO 6
<211> LENGTH: 11
<212> TYPE: PRT
<213> ORGANISM: Mus musculus

<400> SEQUENCE: 6

Arg Ala Ser Gln Asp Ile Ser Asn Tyr Leu Asn
1               5                   10

<210> SEQ ID NO 7
<211> LENGTH: 7
<212> TYPE: PRT
<213> ORGANISM: Mus musculus

<400> SEQUENCE: 7

Phe Ala Ser Arg Leu His Ser
1               5

<210> SEQ ID NO 8
<211> LENGTH: 9
<212> TYPE: PRT
<213> ORGANISM: Mus musculus

<400> SEQUENCE: 8

Gln Gln Gly Ser Thr Leu Pro Trp Thr
1               5

<210> SEQ ID NO 9
<211> LENGTH: 112
<212> TYPE: PRT
<213> ORGANISM: Mus musculus

<400> SEQUENCE: 9

Gln Val Gln Leu Gln Gln Pro Gly Ala Asp Leu Val Lys Pro Gly Ala
1               5                   10                  15

Ser Val Lys Met Ser Cys Lys Ala Ser Gly Tyr Ile Leu Thr Thr Tyr
                20                  25                  30

Trp Ile Thr Trp Val Lys Gln Arg Pro Gly Gln Gly Leu Glu Trp Ile
            35                  40                  45

Gly Asp Ile His Pro Gly Ser Gly Ser Thr Lys Tyr Asn Glu Lys Phe

```
                50                  55                  60
Lys Ser Lys Ala Thr Leu Thr Val Asp Thr Ser Ser Thr Ala Tyr
 65                  70                  75                  80

Met Gln Leu Thr Arg Leu Ser Ser Glu Asp Ser Ala Val Tyr Tyr Cys
                     85                  90                  95

Ala Arg Arg Asp Tyr Trp Gly Gln Gly Thr Thr Leu Thr Val Ser Ser
                100                 105                 110
```

<210> SEQ ID NO 10
<211> LENGTH: 112
<212> TYPE: PRT
<213> ORGANISM: Mus musculus

<400> SEQUENCE: 10

```
Asp Val Leu Met Thr Gln Ser Pro Leu Ser Leu Pro Val Ser Leu Gly
 1               5                  10                  15

Asp Gln Ala Ser Ile Ser Cys Arg Ser Ser Gln Asn Ile Val Asn Ser
                20                  25                  30

Gln Gly Asn Thr Tyr Leu Glu Trp Tyr Leu Gln Lys Pro Gly Glu Ser
            35                  40                  45

Pro Lys Leu Leu Ile Tyr Lys Val Thr Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Ala
                 85                  90                  95

Ser Leu Val Pro Trp Thr Phe Gly Gly Gly Thr Lys Leu Glu Ile Lys
                100                 105                 110
```

<210> SEQ ID NO 11
<211> LENGTH: 10
<212> TYPE: PRT
<213> ORGANISM: Mus musculus

<400> SEQUENCE: 11

```
Gly Tyr Ile Leu Thr Thr Tyr Trp Ile Thr
 1               5                  10
```

<210> SEQ ID NO 12
<211> LENGTH: 17
<212> TYPE: PRT
<213> ORGANISM: Mus musculus

<400> SEQUENCE: 12

```
Asp Ile His Pro Gly Ser Gly Ser Thr Lys Tyr Asn Glu Lys Phe Lys
 1               5                  10                  15

Ser
```

<210> SEQ ID NO 13
<211> LENGTH: 3
<212> TYPE: PRT
<213> ORGANISM: Mus musculus

<400> SEQUENCE: 13

```
Arg Asp Tyr
 1
```

<210> SEQ ID NO 14
<211> LENGTH: 16
<212> TYPE: PRT

<213> ORGANISM: Mus musculus

<400> SEQUENCE: 14

Arg Ser Ser Gln Asn Ile Val Asn Ser Gln Gly Asn Thr Tyr Leu Glu
1               5                   10                  15

<210> SEQ ID NO 15
<211> LENGTH: 7
<212> TYPE: PRT
<213> ORGANISM: Mus musculus

<400> SEQUENCE: 15

Lys Val Thr Asn Arg Phe Ser
1               5

<210> SEQ ID NO 16
<211> LENGTH: 9
<212> TYPE: PRT
<213> ORGANISM: Mus musculus

<400> SEQUENCE: 16

Phe Gln Ala Ser Leu Val Pro Trp Thr
1               5

<210> SEQ ID NO 17
<211> LENGTH: 446
<212> TYPE: PRT
<213> ORGANISM: Artificial Sequence
<220> FEATURE:
<223> OTHER INFORMATION: Humanized antibody

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asp Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Ser Asn Tyr Asn Glu Lys Ile
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Gly Phe Thr Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr

```
            210                 215                 220
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 18
<211> LENGTH: 214
<212> TYPE: PRT
<213> ORGANISM: Artificial Sequence
<220> FEATURE:
<223> OTHER INFORMATION: Humanized antibody

<400> SEQUENCE: 18

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Ile Lys Leu Leu Leu
        35                  40                  45

Asn Phe Ala Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Ser Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                    130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 19
<211> LENGTH: 442
<212> TYPE: PRT
<213> ORGANISM: Artificial Sequence
<220> FEATURE:
<223> OTHER INFORMATION: Humanized antibody

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Leu Thr Thr Tyr
                20                  25                  30

Trp Ile Thr Trp Val Arg Gln Ala Pro Gly Gln Gly Leu Glu Trp Met
                35                  40                  45

Gly Asp Ile His Pro Gly Ser Gly Ser Thr Lys Tyr Asn Glu Lys Phe
50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Arg Asp Tyr Trp Gly Gln Gly Thr Thr Val Thr Val Ser Ser
                100                 105                 110

Ala Ser Thr Lys Gly Pro Ser Val Phe Pro Leu Ala Pro Ser Ser Lys
                115                 120                 125

Ser Thr Ser Gly Gly Thr Ala Ala Leu Gly Cys Leu Val Lys Asp Tyr
                130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
                180                 185                 190

Tyr Ile Cys Asn Val Asn His Lys Pro Ser Asn Thr Lys Val Asp Lys
                195                 200                 205

Lys Val Glu Pro Lys Ser Cys Asp Lys Thr His Thr Cys Pro Pro Cys
                210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
                260                 265                 270

Tyr Val Asp Gly Val Glu Val His Asn Ala Lys Thr Lys Pro Arg Glu
```

```
            275                 280                 285
Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 20
<211> LENGTH: 219
<212> TYPE: PRT
<213> ORGANISM: Artificial Sequence
<220> FEATURE:
<223> OTHER INFORMATION: Humanized antibody

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val Asn Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Lys Val Thr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser Leu Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
                195                 200                 205
Pro Val Thr Lys Ser Phe Asn Arg Gly Glu Cys
    210                 215
```

```
<210> SEQ ID NO 21
<211> LENGTH: 98
<212> TYPE: PRT
<213> ORGANISM: Homo sapien

<400> SEQUENCE: 21
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

```
<210> SEQ ID NO 22
<211> LENGTH: 95
<212> TYPE: PRT
<213> ORGANISM: Homo sapien

<400> SEQUENCE: 22
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95
```

```
<210> SEQ ID NO 23
<211> LENGTH: 98
<212> TYPE: PRT
<213> ORGANISM: Homo sapien

<400> SEQUENCE: 23
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60
```

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 24
<211> LENGTH: 100
<212> TYPE: PRT
<213> ORGANISM: Homo sapien

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 25
<211> LENGTH: 116
<212> TYPE: PRT
<213> ORGANISM: Artificial Sequence
<220> FEATURE:
<223> OTHER INFORMATION: Heavy chain variable region of humanized
      antibody

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Ser Asn Tyr Asn Glu Lys Ile
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Gly Phe Thr Tyr Trp Gly Gln Gly Thr Leu Val
            100                 105                 110

Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: Heavy chain variable region of humanized
``` antibody

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asp Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Ser Asn Tyr Asn Glu Lys Ile
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Gly Phe Thr Tyr Trp Gly Gln Gly Thr Leu Val
            100                 105                 110

Thr Val Ser Ser
        115

<210> SEQ ID NO 27
<211> LENGTH: 126
<212> TYPE: PRT
<213> ORGANISM: Artificial Sequence
<220> FEATURE:
<223> OTHER INFORMATION: Heavy chain variable region of humanized
      antibody

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asp Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Gly Ser Asn Tyr Asn Glu Lys Ile
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Gly Phe Thr Tyr Trp Gly Gln Gly Thr Leu Val
            100                 105                 110

Thr Val Ser Ser Phe Gly Gln Gly Thr Lys Leu Glu Ile Lys
        115                 120                 125

<210> SEQ ID NO 28
<211> LENGTH: 112
<212> TYPE: PRT
<213> ORGANISM: Artificial Sequence
<220> FEATURE:
<223> OTHER INFORMATION: Heavy chain variable region of humanized
      antibody

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

```
Trp Ile Thr Trp Val Arg Gln Ala Pro Gly Gln Gly Leu Glu Trp Met
            35                  40                  45

Gly Asp Ile His Pro Gly Ser Gly Ser Thr Lys Tyr Asn Glu Lys Phe
 50                  55                  60

Lys Ser Arg Val Thr Met Thr Val Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Arg Asp Tyr Trp Gly Gln Gly Thr Thr Val Thr Val Ser Ser
                100                 105                 110
```

<210> SEQ ID NO 29
<211> LENGTH: 112
<212> TYPE: PRT
<213> ORGANISM: Artificial Sequence
<220> FEATURE:
<223> OTHER INFORMATION: Heavy chain variable region of humanized antibody

<400> SEQUENCE: 29

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                20                  25                  30

Trp Ile Thr Trp Val Arg Gln Ala Pro Gly Gln Gly Leu Glu Trp Met
            35                  40                  45

Gly Asp Ile His Pro Gly Ser Gly Ser Thr Lys Tyr Asn Glu Lys Phe
 50                  55                  60

Lys Ser Arg Val Thr Leu Thr Val Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Arg Asp Tyr Trp Gly Gln Gly Thr Thr Val Thr Val Ser Ser
                100                 105                 110
```

<210> SEQ ID NO 30
<211> LENGTH: 112
<212> TYPE: PRT
<213> ORGANISM: Artificial Sequence
<220> FEATURE:
<223> OTHER INFORMATION: Heavy chain variable region of humanized antibody

<400> SEQUENCE: 30

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Leu Thr Thr Tyr
                20                  25                  30

Trp Ile Thr Trp Val Arg Gln Ala Pro Gly Gln Gly Leu Glu Trp Met
            35                  40                  45

Gly Asp Ile His Pro Gly Ser Gly Ser Thr Lys Tyr Asn Glu Lys Phe
 50                  55                  60

Lys Ser Arg Val Thr Leu Thr Val Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Arg Asp Tyr Trp Gly Gln Gly Thr Thr Val Thr Val Ser Ser
                100                 105                 110
```

```
<210> SEQ ID NO 31
<211> LENGTH: 107
<212> TYPE: PRT
<213> ORGANISM: Artificial Sequence
<220> FEATURE:
<223> OTHER INFORMATION: Light chain variable region of humanized
      antibody

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Leu
        35                  40                  45

Asn Phe Ala Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Ser Thr Leu Pro Trp
                85                  90                  95

Thr Phe Gly Gly Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Light chain variable region of humanized
      antibody

<400> SEQUENCE: 32

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Leu
        35                  40                  45

Asn Phe Ala Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Ser Thr Leu Pro Trp
                85                  90                  95

Thr Phe Gly Gly Gly Thr Lys Val Glu Ile Lys
            100                 105

<210> SEQ ID NO 33
<211> LENGTH: 107
<212> TYPE: PRT
<213> ORGANISM: Artificial Sequence
<220> FEATURE:
<223> OTHER INFORMATION: Light chain variable region of humanized
      antibody

<400> SEQUENCE: 33

Asp Ile Gln Leu Thr Gln Ser Pro Ser Ser Leu Ser Ala Ser Val Gly
1               5                   10                  15
```

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Ile Lys Leu Leu Leu
        35                  40                  45

Asn Phe Ala Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Ser Thr Leu Pro Trp
                85                  90                  95

Thr Phe Gly Gly Gly Thr Lys Val Glu Ile Lys
            100                 105

<210> SEQ ID NO 34
<211> LENGTH: 112
<212> TYPE: PRT
<213> ORGANISM: Artificial Sequence
<220> FEATURE:
<223> OTHER INFORMATION: Light chain variable region of humanized
      antibody

<400> SEQUENCE: 34

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val Asn Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Lys Val Thr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser Leu Val Pro Trp Thr Phe Gly Gly Gly Thr Lys Val Glu Ile Lys
            100                 105                 110

<210> SEQ ID NO 35
<211> LENGTH: 112
<212> TYPE: PRT
<213> ORGANISM: Artificial Sequence
<220> FEATURE:
<223> OTHER INFORMATION: Light chain variable region of humanized
      antibody

<400> SEQUENCE: 35

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val Asn Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Lys Val Thr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser Leu Val Pro Trp Thr Phe Gly Gly Gly Thr Lys Val Glu Ile Lys
            100                 105                 110

<210> SEQ ID NO 36
<211> LENGTH: 112
<212> TYPE: PRT
<213> ORGANISM: Artificial Sequence
<220> FEATURE:
<223> OTHER INFORMATION: Light chain variable region of humanized
      antibody

<400> SEQUENCE: 36

Asp Val Leu Met Thr Gln Ser Pro Leu Ser Leu Pro Val Thr Pro Gly
1               5                   10                  15

Glu Pro Ala Ser Ile Ser Cys Arg Ser Ser Gln Asn Ile Val Asn Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Lys Val Thr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser Leu Val Pro Trp Thr Phe Gly Gly Gly Thr Lys Val Glu Ile Lys
            100                 105                 110

<210> SEQ ID NO 37
<211> LENGTH: 116
<212> TYPE: PRT
<213> ORGANISM: Mus musculus

<400> SEQUENCE: 37

Gln Val Arg Leu Gln Gln Ser Gly Ala Glu Leu Val Arg Pro Gly Thr
1               5                   10                  15

Ser Met Arg Val Ser Cys Lys Ala Ser Gly Tyr Ala Phe Thr Asn Tyr
            20                  25                  30

Leu Ile Asn Trp Val Lys Gln Arg Pro Gly Gln Gly Leu Glu Trp Ile
        35                  40                  45

Gly Ile Leu Asn Pro Gly Ser Gly Gly Thr Asn Tyr Asn Glu Asn Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ile Arg Gly Ser Pro Gly Phe Ala Tyr Trp Gly Gln Gly Thr Leu Val
            100                 105                 110

Thr Val Ser Ala
        115

<210> SEQ ID NO 38
<211> LENGTH: 107
<212> TYPE: PRT
<213> ORGANISM: Mus musculus

<400> SEQUENCE: 38

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Ile Tyr

```
                20                  25                  30
Leu Asn Trp Tyr Gln Gln Lys Pro Asp Gly Thr Val Lys Leu Leu Ile
                35                  40                  45

Tyr Ser Thr Ser Gly Leu His Ser Gly Val Pro Ser Arg Phe Asn Gly
            50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Tyr
                85                  90                  95

Thr Phe Gly Gly Gly Thr Lys Leu Glu Ile Lys
            100                 105
```

<210> SEQ ID NO 39
<211> LENGTH: 10
<212> TYPE: PRT
<213> ORGANISM: Mus musculus

<400> SEQUENCE: 39

```
Gly Tyr Ala Phe Thr Asn Tyr Leu Ile Asn
1               5                   10
```

<210> SEQ ID NO 40
<211> LENGTH: 17
<212> TYPE: PRT
<213> ORGANISM: Mus musculus

<400> SEQUENCE: 40

```
Ile Leu Asn Pro Gly Ser Gly Gly Thr Asn Tyr Asn Glu Asn Phe Lys
1               5                   10                  15

Asp
```

<210> SEQ ID NO 41
<211> LENGTH: 7
<212> TYPE: PRT
<213> ORGANISM: Mus musculus

<400> SEQUENCE: 41

```
Gly Ser Pro Gly Phe Ala Tyr
1               5
```

<210> SEQ ID NO 42
<211> LENGTH: 11
<212> TYPE: PRT
<213> ORGANISM: Mus musculus

<400> SEQUENCE: 42

```
Arg Ala Ser Gln Asp Ile Asn Ile Tyr Leu Asn
1               5                   10
```

<210> SEQ ID NO 43
<211> LENGTH: 7
<212> TYPE: PRT
<213> ORGANISM: Mus musculus

<400> SEQUENCE: 43

```
Ser Thr Ser Gly Leu His Ser
1               5
```

<210> SEQ ID NO 44
<211> LENGTH: 9
<212> TYPE: PRT
<213> ORGANISM: Mus musculus

```
<400> SEQUENCE: 44

Gln Gln Gly Tyr Thr Leu Pro Tyr Thr
1               5

<210> SEQ ID NO 45
<211> LENGTH: 116
<212> TYPE: PRT
<213> ORGANISM: Mus musculus

<400> SEQUENCE: 45

Gln Val Gln Val Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
            35                  40                  45

Gly Val Ile Asn Pro Glu Phe Gly Gly Thr Asn Tyr Asn Glu Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Gly Gly Phe Thr Tyr Trp Gly Gln Gly Thr Leu Val
            100                 105                 110

Thr Val Ser Ala
        115

<210> SEQ ID NO 46
<211> LENGTH: 107
<212> TYPE: PRT
<213> ORGANISM: Mus musculus

<400> SEQUENCE: 46

His Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Ser His
                20                  25                  30

Leu Asn Trp Tyr Gln Gln Lys Pro Asp Gly Thr Val Lys Leu Leu Ile
            35                  40                  45

Ser Tyr Thr Ser Arg Leu His Ser Gly Val Pro Ser Arg Phe Ser Gly
        50                  55                  60

Ser Gly Ser Gly Ala Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 47
<211> LENGTH: 10
<212> TYPE: PRT
<213> ORGANISM: Mus musculus

<400> SEQUENCE: 47

Gly Tyr Ala Phe Thr Asn Tyr Leu Ile Glu
1               5                   10
```

```
<210> SEQ ID NO 48
<211> LENGTH: 17
<212> TYPE: PRT
<213> ORGANISM: Mus musculus

<400> SEQUENCE: 48

Val Ile Asn Pro Glu Phe Gly Gly Thr Asn Tyr Asn Glu Lys Phe Lys
1               5                   10                  15

Gly

<210> SEQ ID NO 49
<211> LENGTH: 7
<212> TYPE: PRT
<213> ORGANISM: Mus musculus

<400> SEQUENCE: 49

Gly Gly Gly Gly Phe Thr Tyr
1               5

<210> SEQ ID NO 50
<211> LENGTH: 11
<212> TYPE: PRT
<213> ORGANISM: Mus musculus

<400> SEQUENCE: 50

Arg Ala Ser Gln Asp Ile Ser Ser His Leu Asn
1               5                   10

<210> SEQ ID NO 51
<211> LENGTH: 7
<212> TYPE: PRT
<213> ORGANISM: Mus musculus

<400> SEQUENCE: 51

Tyr Thr Ser Arg Leu His Ser
1               5

<210> SEQ ID NO 52
<211> LENGTH: 9
<212> TYPE: PRT
<213> ORGANISM: Mus musculus

<400> SEQUENCE: 52

Gln Gln Gly Asn Thr Leu Pro Trp Thr
1               5

<210> SEQ ID NO 53
<211> LENGTH: 119
<212> TYPE: PRT
<213> ORGANISM: Mus musculus

<400> SEQUENCE: 53

Gln Val Arg Leu Lys Gln Ser Gly Ala Glu Leu Val Arg Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Gly Ile Tyr Pro Gly Thr Gly Asn Thr Tyr Tyr Asn Glu Lys Phe
    50                  55                  60

Lys Gly Lys Ala Thr Leu Thr Ala Glu Arg Ser Ser Ser Thr Ala Tyr
65                  70                  75                  80
```

Met Gln Leu Thr Ser Leu Thr Ser Glu Asp Ser Ala Val Tyr Phe Cys
                85                  90                  95

Thr Arg Arg Gly Leu Pro Ser Leu Cys Phe Asp Tyr Trp Gly Gln Gly
            100                 105                 110

Thr Thr Leu Thr Val Ser Ser
            115

<210> SEQ ID NO 54
<211> LENGTH: 107
<212> TYPE: PRT
<213> ORGANISM: Mus musculus

<400> SEQUENCE: 54

Asp Phe Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Pro
                85                  90                  95

Thr Phe Gly Gly Gly Thr Lys Leu Glu Ile Lys
            100                 105

<210> SEQ ID NO 55
<211> LENGTH: 10
<212> TYPE: PRT
<213> ORGANISM: Mus musculus

<400> SEQUENCE: 55

Gly Tyr Thr Phe Thr Asp Tyr Tyr Ile Asn
1               5                   10

<210> SEQ ID NO 56
<211> LENGTH: 17
<212> TYPE: PRT
<213> ORGANISM: Mus musculus

<400> SEQUENCE: 56

Gly Ile Tyr Pro Gly Thr Gly Asn Thr Tyr Tyr Asn Glu Lys Phe Lys
1               5                   10                  15

Gly

<210> SEQ ID NO 57
<211> LENGTH: 10
<212> TYPE: PRT
<213> ORGANISM: Mus musculus

<400> SEQUENCE: 57

Arg Gly Leu Pro Ser Leu Cys Phe Asp Tyr
1               5                   10

<210> SEQ ID NO 58
<211> LENGTH: 11
<212> TYPE: PRT
<213> ORGANISM: Mus musculus

```
<400> SEQUENCE: 58

Ser Ala Ser Gln Gly Ile Ser Asn Tyr Leu Asn
1               5                   10

<210> SEQ ID NO 59
<211> LENGTH: 7
<212> TYPE: PRT
<213> ORGANISM: Mus musculus

<400> SEQUENCE: 59

Tyr Thr Ser Ser Leu His Ser
1               5

<210> SEQ ID NO 60
<211> LENGTH: 9
<212> TYPE: PRT
<213> ORGANISM: Mus musculus

<400> SEQUENCE: 60

Gln Gln Tyr Ser Lys Leu Pro Pro Thr
1               5
```

ANTI-CD40 ANTIBODY, ANTIGEN BINDING FRAGMENT THEREOF AND MEDICAL USE THEREOF

CROSS-REFERENCE TO RELATED APPLICATIONS

The present application is a National Stage Application under 35 U.S.C. § 371 and claims the benefit of International Patent Application No. PCT/CN2018/089252, filed on May 31, 2018, which claims priority of Chinese Patent Application No. CN201710402559.0, filed on Jun. 1, 2017. The entire contents of the aforementioned applications are hereby incorporated by reference.

FIELD OF THE INVENTION

The present invention relates to an anti-CD40 antibody, an antigen binding fragment thereof, a chimeric antibody or a humanized antibody comprising CDR regions of the anti-CD40 antibody, and a pharmaceutical composition comprising a human anti-CD40 antibody and antigen binding fragment thereof, and a use thereof as an anticancer drug.

BACKGROUND OF THE INVENTION

As one of the top killers of health, cancer is a significant challenge that human society will face in a long term future. Therapies such as traditional surgery, chemotherapy and radiotherapy often have limited effect in the treatment of disseminated solid tumors. Tumor immunotherapy, especially T cell tumor immunotherapy is a hot spot in the field of tumor therapy. Tumor immunotherapy kills tumors by fully activating killer T cells in patients with tumor, which may be the most effective and safest way to treat tumors. Tumor immunotherapy currently has shown promising prospects in the treatment of several different types of cancer, including disseminated metastatic tumors.

Activation of T cells in human body employs a system including two signaling pathways. In addition to providing a first signal to T cells by presenting MHC-antigen peptides through antigen presenting cell (APC), a series of co-stimulatory molecules are required to provide a second signal, thus enabling normal immune responses of T cells. This dual-signaling pathway system plays a crucial role in the balance of the immune system in vivo, which strictly regulates the body to activate different immune responses to self and non-self antigens. The absence of the second signal provided by a co-stimulatory molecule will lead to failure in T cells responses or loss of sustained specific immune responses, thus resulting in immune tolerance. Therefore, the second signaling pathway plays a very critical role in regulating the whole process of immune response.

CD40 is one of the glycoproteins expressed on the cell surface. It is a 48 kDa of type I membrane intrinsic glycoprotein, which belongs to the tumor necrosis factor receptor (TNFR) superfamily and plays a crucial role in the immune system. It is expressed in a variety of immune cells, such as B cells, dendritic cells, monocytes and macrophages. When signal transduction is mediated by CD40, specialized antigen presenting cells will be activated. The natural ligand of CD40 is designated CD154 or CD40L and is known to be predominantly expressed in mature T lymphocytes. CD40L-mediated signaling transduction can trigger a number of cellular biological events, including activation and proliferation of immune cells, and production of cytokines and chemokines. CD40 signaling is extremely crucial for T cell-dependent immune responses, especially in the context of tumor environment. CD40-stimulated dendritic cells are capable of activating tumor-specific effector T cells, which have the potential to eradicate tumor cells.

Expression of CD40 has been found in a variety of normal cells and tumor cells including B lymphocytes. For example, melanoma is a tumor expressing CD40, while 30%-70% of solid tumors also express CD40. It is currently known that activation of CD40 can effectively trigger anti-tumor responses (Tong et al, *Cancer Gene Therapy*, 2003, 10: 1-13), including immune activation of tumor-specific T cell responses, direct apoptosis of CD40-positive tumors and humoral reaction of ADCC caused by stimulation. Moreover, observed tumor eradication is strongly associated with the occurrence of cytotoxic T lymphocytes with tumor specificity. Meanwhile, it also should not be ignored that systemic administration of CD40 antibodies generally associates with a variety of side effects such as shock syndrome and cytokine release syndrome (van Mierlo et al, *Proc. Natl. Acad. Sci. USA*, 2002, 99: 5561-5566).

Currently a number of international pharmaceutical companies are developing monoclonal antibodies against CD40, which specifically stimulate immune activation, maximizing patients' own immune system response to tumors, thereby achieving the purpose of killing tumor cells. Related patents include CN1198647, CN1369015, CN1582165, CN100430419, CN101014386, CN101237882, CN101289510, CN101490086, CN103842382, CN104918957, WO2002028904, WO2011123489, WO2012149356, WO2013034904, WO2015091853, WO2016196314, WO2017040932 and WO2017004006 etc. To date, anti-CD40 antibodies of Pfizer (related products have been licensed to Roche), Alligator and other companies that were found to have good tumor killing effects in preclinical animal models has entered a Phase I clinical trials.

The present invention aim to provide an anti-CD40 antibody with high affinity, high selectivity and high biological activity, and a cancer therapeutic drug/composition and method thereof for activating immune responses by stimulating CD40 and pathway thereof.

SUMMARY OF THE INVENTION

This invention provides an anti-CD40 antibody or antigen binding fragment thereof, comprising: an antibody light chain variable region comprising at least one LCDR selected from the group consisting of SEQ ID NO: 6, SEQ ID NO: 7, SEQ ID NO: 8, SEQ ID NO: 14, SEQ ID NO: 15, SEQ ID NO: 16, SEQ ID NO: 42, SEQ ID NO: 43, SEQ ID NO: 44, SEQ ID NO: 50, SEQ ID NO: 51, SEQ ID NO: 52, SEQ ID NO: 58, SEQ ID NO: 59 or SEQ ID NO: 60; and/or, an antibody heavy chain variable region comprising at least one HCDR selected from the group consisting of SEQ ID NO: 3, SEQ ID NO: 4, SEQ ID NO: 5, SEQ ID NO: 11, SEQ ID NO: 12, SEQ ID NO: 13, SEQ ID NO: 39, SEQ ID NO: 40, SEQ ID NO: 41, SEQ ID NO: 47, SEQ ID NO: 48, SEQ ID NO: 49, SEQ ID NO: 55 or SEQ ID NO: 56 or SEQ ID NO: 57.

In a preferable embodiment of this invention, provided is an anti-CD40 antibody or antigen binding fragment thereof as described above, wherein the antibody light chain variable region comprises a LCDR1 having the sequence of SEQ ID NO: 6, SEQ ID NO: 14, SEQ ID NO: 42, SEQ ID NO: 50 or SEQ ID NO: 58.

In a preferable embodiment of this invention, provided is an anti-CD40 antibody or antigen binding fragment thereof as described above, wherein the antibody light chain variable region comprises a LCDR2 having the sequence of SEQ ID NO: 7, SEQ ID NO: 15, SEQ ID NO: 43, SEQ ID NO: 51 or SEQ ID NO: 59.

In a preferable embodiment of this invention, provided is an anti-CD40 antibody or antigen binding fragment thereof as described above, wherein the antibody light chain variable region comprises a LCDR3 having the sequence of SEQ ID NO: 8, SEQ ID NO: 16, SEQ ID NO: 44, SEQ ID NO: 52 or SEQ ID NO: 60.

In a preferable embodiment of this invention, provided is an anti-CD40 antibody or antigen binding fragment thereof as described above, wherein the antibody light chain variable region comprises a HCDR1 having the sequence of SEQ ID NO: 3, SEQ ID NO: 11, SEQ ID NO: 39, SEQ ID NO: 47 or SEQ ID NO: 55.

In a preferable embodiment of this invention, provided is an anti-CD40 antibody or antigen binding fragment thereof as described above, wherein the antibody light chain variable region comprises a HCDR2 having the sequence of SEQ ID NO: 4, SEQ ID NO: 12, SEQ ID NO: 40, SEQ ID NO: 48 or SEQ ID NO: 56.

In a preferable embodiment of this invention, provided is an anti-CD40 antibody or antigen binding fragment thereof as described above, wherein the antibody light chain variable region comprises a HCDR3 having the sequence of SEQ ID NO: 5, SEQ ID NO: 13, SEQ ID NO: 41, SEQ ID NO: 49 or SEQ ID NO: 57.

In a preferable embodiment of this invention, provided is an anti-CD40 antibody or antigen binding fragment thereof as described above, wherein the antibody light chain variable region comprises a LCDR1, a LCDR2 and a LCDR3 having the sequence of SEQ ID NO: 6, SEQ ID NO: 7 and SEQ ID NO: 8, respectively.

In a preferable embodiment of this invention, provided is an anti-CD40 antibody or antigen binding fragment thereof as described above, wherein the antibody light chain variable region comprises a LCDR1, a LCDR2 and a LCDR3 having the sequence of SEQ ID NO: 14, SEQ ID NO: 15 and SEQ ID NO: 16, respectively.

In a preferable embodiment of this invention, provided is an anti-CD40 antibody or antigen binding fragment thereof as described above, wherein the antibody light chain variable region comprises a LCDR1, a LCDR2 and a LCDR3 having the sequence of SEQ ID NO: 42, SEQ ID NO: 43 and SEQ ID NO: 44, respectively.

In a preferable embodiment of this invention, provided is an anti-CD40 antibody or antigen binding fragment thereof as described above, wherein the antibody light chain variable region comprises a LCDR1, a LCDR2 and a LCDR3 having the sequence of SEQ ID NO: 50, SEQ ID NO: 51, and SEQ ID NO: 52, respectively.

In a preferable embodiment of this invention, provided is an anti-CD40 antibody or antigen binding fragment thereof as described above, wherein the antibody light chain variable region comprises a LCDR1, a LCDR2 and a LCDR3 having the sequence of SEQ ID NO: 58, SEQ ID NO: 59, and SEQ ID NO: 60, respectively.

In a preferable embodiment of this invention, provided is an anti-CD40 antibody or antigen binding fragment thereof as described above, wherein the antibody heavy chain variable region comprises a HCDR1, a HCDR2 and a HCDR3 having the sequence of SEQ ID NO: 3, SEQ ID NO: 4 and SEQ ID NO: 5, respectively.

In a preferable embodiment of this invention, provided is an anti-CD40 antibody or antigen binding fragment thereof as described above, wherein the antibody heavy chain variable region comprises a HCDR1, a HCDR2 and a HCDR3 having the sequence of SEQ ID NO: 11, SEQ ID NO: 12 and SEQ ID NO: 13, respectively.

In a preferable embodiment of this invention, provided is an anti-CD40 antibody or antigen binding fragment thereof as described above, wherein the antibody heavy chain variable region comprises a HCDR1, a HCDR2 and a HCDR3 having the sequence of SEQ ID NO: 39, SEQ ID NO: 40 and SEQ ID NO: 41, respectively.

In a preferable embodiment of this invention, provided is an anti-CD40 antibody or antigen binding fragment thereof as described above, wherein the antibody heavy chain variable region comprises a HCDR1, a HCDR2 and a HCDR3 having the sequence of SEQ ID NO: 47, SEQ ID NO: 48, and SEQ ID NO: 49, respectively.

In a preferable embodiment of this invention, provided is an anti-CD40 antibody or antigen binding fragment thereof as described above, wherein the antibody heavy chain variable region comprises a HCDR1, a HCDR2 and a HCDR3 having the sequence of SEQ ID NO: 55, SEQ ID NO: 56, and SEQ ID NO: 57, respectively.

In a preferable embodiment of this invention, provided is an anti-CD40 antibody or antigen binding fragment thereof as described above, wherein the antibody light chain variable region comprises a LCDR1, a LCDR2 and a LCDR3 having the sequence of SEQ ID NO: 6, SEQ ID NO: 7 and SEQ ID NO: 8, respectively, or a LCDR1, a LCDR2 and a LCDR3 having the sequence of SEQ ID NO: 14, SEQ ID NO: 15 and SEQ ID NO: 16, respectively, or a LCDR1, a LCDR2 and a LCDR3 having the sequence of SEQ ID NO: 42, SEQ ID NO: 43 and SEQ ID NO: 44, respectively, or a LCDR1, a LCDR2, and a LCDR3 having the sequence of SEQ ID NO: 50, SEQ ID NO: 51, and SEQ ID NO: 52, respectively, or LCDR1, LCDR2, and LCDR3 having the sequence of SEQ ID NO: 58, SEQ ID NO: 59, and SEQ ID NO: 60, respectively; and, the antibody heavy chain variable region comprises a HCDR1, a HCDR2 and a HCDR3 having the sequence of SEQ ID NO: 3, SEQ ID NO: 4 and SEQ ID NO: 5, respectively, or a HCDR1, a HCDR2 and a HCDR3 having the sequence of SEQ ID NO: 11, SEQ ID NO: 12 and SEQ ID NO: 13, respectively, or a HCDR1, a HCDR2 and a HCDR3 having the sequence of SEQ ID NO: 39, SEQ ID NO: 40 and SEQ ID NO: 41, respectively, or a HCDR1, a HCDR2, and a HCDR3 having the sequence of SEQ ID NO: 47, SEQ ID NO: 48, and SEQ ID NO: 49, respectively, or a HCDR1, a HCDR2, and a HCDR3 having the sequence of SEQ ID NO: 55, SEQ ID NO: 56, and SEQ ID NO: 57, respectively.

A particularly preferable anti-CD40 antibody or antigen binding fragment thereof may be selected from the group consisting of:

(1) an antibody light chain variable region comprises a LCDR1, a LCDR2 and a LCDR3 having the sequence of SEQ ID NO: 6, SEQ ID NO: 7 and SEQ ID NO: 8, respectively; and an antibody heavy chain variable region comprises a HCDR1, a HCDR2 and a HCDR3 having the sequence of SEQ ID NO: 3, SEQ ID NO: 4 and SEQ ID NO: 5, respectively;

(2) an antibody light chain variable region comprises a LCDR1, a LCDR2 and a LCDR3 having the sequence of SEQ ID NO: 14, SEQ ID NO: 15 and SEQ ID NO: 16, respectively; and an antibody heavy chain variable region comprises a HCDR1, a HCDR2 and a HCDR3 having the sequence of SEQ ID NO: 11, SEQ ID NO: 12 and SEQ ID NO: 13, respectively;

(3) an antibody light chain variable region comprises a LCDR1, a LCDR2 and a LCDR3 having the sequence of SEQ ID NO: 42, SEQ ID NO: 43 and SEQ ID NO: 44, respectively; and an antibody heavy chain variable region comprises a HCDR1, a HCDR2 and a HCDR3 having the sequence of SEQ ID NO: 39, SEQ ID NO: 40 and SEQ ID NO: 41, respectively;

(4) an antibody light chain variable region comprises a LCDR1, a LCDR2, and a LCDR3 having the sequence of SEQ ID NO: 50, SEQ ID NO: 51, and SEQ ID NO: 52, respectively; and an antibody heavy chain variable region comprises a HCDR1, a HCDR2, and a HCDR3 having the sequence of SEQ ID NO: 47, SEQ ID NO: 48, and SEQ ID NO: 49, respectively;

(5) an antibody light chain variable region comprises a LCDR1, a LCDR2, and a LCDR3 having the sequence of SEQ ID NO: 58, SEQ ID NO: 59, and SEQ ID NO: 60, respectively; and an antibody heavy chain variable region comprises a HCDR1, a HCDR2, and a HCDR3 having the sequence of SEQ ID NO: 55, SEQ ID NO: 56, and SEQ ID NO: 57, respectively.

In a preferable embodiment of this invention, the antibody light chain variable region has the sequence of SEQ ID NO: 2 or SEQ ID NO: 10; the antibody heavy chain variable region has the sequence of SEQ ID NO: 1 or SEQ ID NO: 9.

The above anti-CD40 antibody or antigen binding fragment thereof can be a murine antibody or a chimeric antibody.

Preferably, the amino acid sequence of heavy chain variable region of the murine antibody or chimeric antibody is shown in SEQ ID NO. 1, and the amino acid sequence of light chain variable region is shown in SEQ ID NO. 2; or the amino acid sequence of heavy chain variable region is shown in SEQ ID NO. 9, and the amino acid sequence of light chain variable region is shown in SEQ ID NO. 10; or the amino acid sequence of light chain variable region (LCVR) is shown in SEQ ID NO. 38, and the amino acid sequence of heavy chain variable region (HCVR) is shown in SEQ ID NO. 37; or the amino acid sequence of light chain variable region (LCVR) is shown in SEQ ID NO. 46, and the amino acid sequence of heavy chain variable region (HCVR) is shown in SEQ ID NO. 45; or the amino acid sequence of light chain variable region (LCVR) is shown in SEQ ID NO. 54, and the amino acid sequence of heavy chain variable region (HCVR) is shown in SEQ ID NO. 53.

In a preferable embodiment of this invention, provided is an anti-CD40 antibody or antigen binding fragment thereof as described above, wherein the antibody or antigen binding fragment thereof is a murine antibody or fragment thereof.

In a preferable embodiment of this invention, provided is a murine antibody or fragment thereof as described above, wherein the antibody light chain variable region further comprises light chain FR region of murine κ, λ, chain or variants thereof.

In a preferable embodiment of this invention, provided is a murine antibody or fragment thereof as described above further comprising light chain constant region of mouse κ, λ, chain or variants thereof.

In a preferable embodiment of this invention, provided is a murine antibody or fragment thereof as described above, wherein the antibody heavy chain variable region further comprises heavy chain FR region of murine IgG1, IgG2, IgG3, IgG4 or variants thereof.

In a preferable embodiment of this invention, provided is a murine antibody or fragment thereof as described above further comprising heavy chain constant region of murine IgG1, IgG2, IgG3, IgG4 or variants thereof.

In a preferable embodiment of this invention, provided is an anti-CD40 antibody or antigen binding fragment thereof as described above, which can be a chimeric antibody or fragment thereof.

In a preferable embodiment of this invention, provided is an anti-CD40 chimeric antibody or fragment thereof as described above, wherein the sequence of the light chain variable region is shown in SEQ ID NO: 2 or SEQ ID NO: 10.

In a preferable embodiment of this invention, provided is an anti-CD40 chimeric antibody or fragment thereof as described above, wherein the sequence of the heavy chain variable region is shown in SEQ ID NO: 1 or SEQ ID NO: 9.

In a preferable embodiment of this invention, provided is an anti-CD40 chimeric antibody or fragment thereof as described above further comprising light chain constant region of human κ, λ, chain or variants thereof.

In a preferable embodiment of this invention, provided is an anti-CD40 chimeric antibody or fragment thereof as described above further comprising heavy chain constant region of human IgG1, IgG2, IgG3, IgG4 or variants thereof.

In a preferable embodiment of this invention, provided is an anti-CD40 antibody or antigen binding fragment thereof as described above, which is a human antibody or fragment thereof.

In a preferable embodiment of this invention, provided is an anti-CD40 antibody or antigen binding fragment thereof as described above, which is a humanized antibody or fragment thereof.

In a preferable embodiment of this invention, provided is an anti-CD40 human antibody or antigen binding fragment thereof as described above, wherein the human antibody has the sequence of SEQ ID NO: 18 or SEQ ID NO: 20 or variants thereof; preferably, the variants have 0-10 mutations of amino acids in the light chain, more preferably, mutations occur at position 2 and 3, and both of the mutated amino acids are preferably I, V or L.

In a preferable embodiment of this invention, provided is an anti-CD40 human antibody or antigen binding fragment thereof as described above, wherein the human antibody has the sequence of SEQ ID NO: 17 or SEQ ID NO: 19 or variants thereof; preferably, the variants have 0-10 mutants of amino acids in the light chain, more preferably, the mutants occur at position 6 and 8, and both of the mutated amino acids are preferably I, A or L.

In a preferable embodiment of this invention, provided is an anti-CD40 human antibody or antigen binding fragment thereof as described above further comprising constant region of IgG1, IgG2, IgG3, IgG4 or variants thereof.

In a preferable embodiment of this invention, provided is an anti-CD40 humanized antibody or antigen binding fragment thereof as described above further comprising light chain FR region of human κ, λ, chain or variants thereof.

In a preferable embodiment of this invention, provided is an anti-CD40 humanized antibody or fragment thereof as described above, wherein the sequence of light chain FR region on light chain variable region of the humanized antibody is derived from light chain IGkV1-33 sequence of human germline shown in SEQ ID NO. 22, or derived from light chain IGkV2-28 sequence of human germline shown in SEQ ID NO. 24.

In a preferable embodiment of this invention, provided is an anti-CD40 humanized antibody or fragment thereof as described above, wherein the sequence of the humanized antibody light chain is the sequence shown in SEQ ID NO. 33 or SEQ ID NO. 34, or variants thereof.

In a preferable embodiment of this invention, provided is an anti-CD40 humanized antibody or fragment thereof as described above, wherein the sequence of the humanized antibody light chain is the sequence shown in SEQ ID NO. 18 or SEQ ID NO. 20, or variants thereof.

In a preferable embodiment of this invention, provided is an anti-CD40 humanized antibody or fragment thereof as described above, wherein the variants of light chain variable region of humanized antibody preferably have 0-10 mutations of amino acids in the light chain, more preferably, the mutations occur at position 2 and 3, and both of the mutated amino acids are preferably I, V or L.

In a preferable embodiment of this invention, provided is an anti-CD40 humanized antibody or fragment thereof as described above further comprising light chain constant region of human κ, λ, chain or variants thereof.

In a preferable embodiment of this invention, provided is an anti-CD40 humanized antibody or fragment thereof as described above further comprising heavy chain FR region of human IgG1, IgG2, IgG3, IgG4 or variants thereof.

In a preferable embodiment of this invention, provided is an anti-CD40 humanized antibody or fragment thereof as described above, wherein the heavy chain FR region of heavy chain variable region is derived from heavy chain IGHV1-69 sequence of human germline shown in SEQ ID NO. 21, or derived from heavy chain IGHV1-2 sequence of human germline shown in SEQ ID NO. 23.

In a preferable embodiment of this invention, provided is an anti-CD40 humanized antibody or fragment thereof as described above, wherein the heavy chain sequence of the humanized antibody is shown in SEQ ID NO: 26 or SEQ ID NO: 30, or variants thereof.

In a preferable embodiment of this invention, provided is an anti-CD40 humanized antibody or fragment thereof as described above, wherein the heavy chain sequence of the humanized antibody is shown in SEQ ID NO: 17 or SEQ ID NO: 19, or variants thereof, preferably, the variants have 0-10 mutations of amino acids in the heavy chain variable region, more preferably, the mutations occur at position 6 and 8, and the mutated amino acids is preferably I, A or L.

In a preferable embodiment of this invention, provided is an anti-CD40 humanized antibody or fragment thereof as described above further comprising heavy chain constant region of human IgG1, IgG2, IgG3, IgG4 or variants thereof, preferably heavy chain FR region of IgG1, IgG2 or IgG4, more preferably heavy chain FR region of IgG1 or IgG2.

In a preferable embodiment of this invention, provided is an anti-CD40 antibody or antigen binding fragment as described above, wherein the antigen binding fragment is a Fab, a Fv, a sFv, F(ab')$_2$, a linear antibody, a single chain antibody, a nanobody, a domain antibodies or a multi-specific antibody.

This invention further provides a DNA sequence encoding the anti-CD40 antibody or antigen binding fragment thereof, the multi-specific antibody, or the single-chain antibody described above.

This invention further provides an expression vector comprising the DNA sequence described above.

This invention further provides host cells transformed with the expression vector described above.

In a preferable embodiment of this invention, provided is the host cells as described above, wherein the host cell is bacterium, preferably *Escherichia coli*.

In a preferable embodiment of this invention, the host cells described above is yeast, preferably *Pichia pastoris*.

In a preferable embodiment of this invention, the host cells described above is mammalian cells, preferably Chinese hamster ovary (CHO) Cell or Human Embryonic Kidney (HEK) 293 cells.

This invention further provides a single-chain antibody comprising the anti-CD40 antibody or antigen binding fragment thereof as described above.

This invention further provides a multi-specific antibody comprising the anti-CD40 antibody or antigen binding fragment thereof as described above.

This invention further provides an antibody-drug conjugate comprising a light chain variable region and/or a heavy chain variable region of the anti-CD40 antibody described above. The antibody-drug conjugates are well known in the art and are formed by the interconnection of antibody-linker-drug (toxin), and known linkers include cleavable linkers, sub cleavable linkers, such as, the linkers including, but not limited to, SMCC, SPDP etc. Toxins are also well known in the art, such as DM1, DM4, MMAE, MMAF, and the like.

This invention further provides a pharmaceutical composition comprising the anti-CD40 antibody or antigen binding fragment thereof, the multi-specific antibody, or the single-chain antibody, and pharmaceutically acceptable excipient, diluent or carrier, as described above.

This invention further provides a use of the anti-CD40 antibody or antigen binding fragment thereof, the multi-specific antibody, the single-chain antibody, the antibody-drug conjugate, or the pharmaceutical composition described above in the manufacture of a medicament for the treatment or prevention of a CD40 or CD40L mediated disease or condition; wherein the disease is preferably cancer; the cancer are most preferably lymphoma, breast cancer, ovarian cancer, prostate cancer, pancreatic cancer, kidney cancer, lung cancer, liver cancer, gastric cancer, colorectal cancer, bladder cancer, rhabdomyosarcoma, esophageal cancer, cervical cancer, multiple myeloma, leukemia, gallbladder cancer, glioblastoma and melanoma.

This invention further provides a method for treating and preventing a CD40 or CD40L mediated disease or condition, the method comprises administering to a subject a therapeutically effective dose of the anti-CD40 antibody or antigen binding fragment thereof, the multi-specific antibody, the single-chain antibody, the antibody-drug conjugate, or the pharmaceutical composition described above, wherein the disease is preferably cancer; the cancer are most preferably lymphoma, breast cancer, ovarian cancer, prostate cancer, pancreatic cancer, kidney cancer, lung cancer, liver cancer, gastric cancer, colorectal cancer, bladder cancer, rhabdomyosarcoma, esophageal cancer, cervical cancer, multiple myeloma, leukemia, gallbladder cancer, glioblastoma and melanoma.

This invention further provides a use of the anti-CD40 antibody or antigen binding fragment thereof, the multi-specific antibody, the single-chain antibody, the antibody-drug conjugate, or the pharmaceutical composition described above in the manufacture of a medicament for improving the symptoms of a patient with an autoimmune disease.

This invention further provides a use of the anti-CD40 antibody or antigen binding fragment thereof, the multi-specific antibody, the single-chain antibody, the antibody-drug conjugate, or the pharmaceutical composition described above in the manufacture of a medicament for improving the symptoms of a patient with an inflammatory disease.

DETAILED DESCRIPTION OF THE PREFERRED EMBODIMENT

1. Definitions

Figure 1:
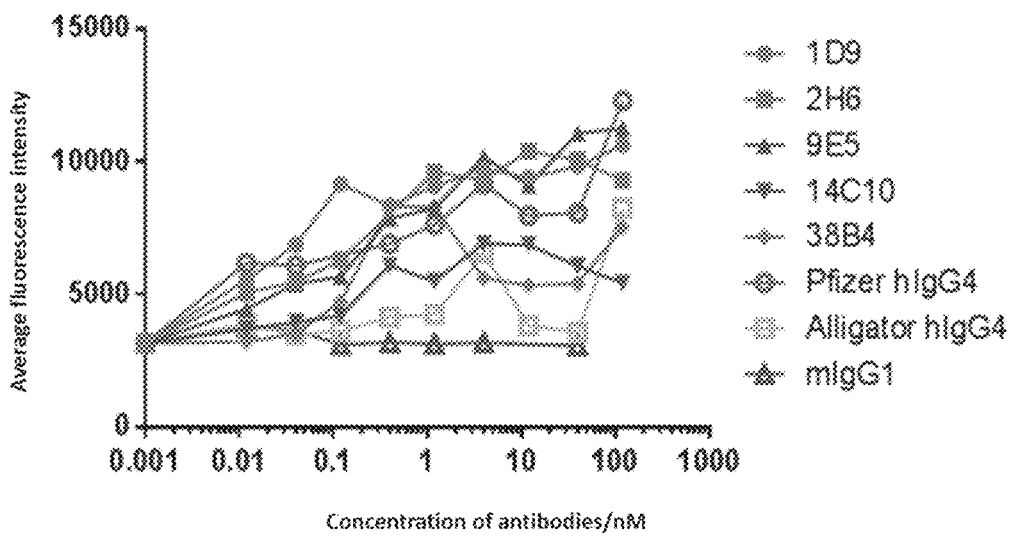
FIG. 1 shows the activation of murine anti-human CD40 antibody on DC cells based on CD80 activating molecules.

In order to make it easier for those skilled in the art to understand the present invention, certain technical and scientific terms are specifically defined below. Unless otherwise obviously clear defined elsewhere in this document, all other technical and scientific terms used herein have the meaning commonly understood by a person skilled in the art to which this invention belongs.

The amino acids three-letter code and single-letter code used in the present invention are described in *J. Biol. Chem*, 243, p3558 (1968).

The term "antibody" as used in the present invention refers to an immunoglobulin, which is a tetrapeptide chain structure formed by linking two identical heavy chains and two identical light chains by interchain disulfide bonds. As the heavy chain constant region of the immunoglobulin has different composition and order of amino acids, the antigenicity of different immunoglobulins is different. Accordingly, immunoglobulins can be classified into five classes, or be referred to as the isotypes of immunoglobulins, namely IgM, IgD, IgG, IgA and IgE, and the corresponding heavy chains of which are μ chain, δ chain, γ chain, α chain and ε chain, respectively. The same type of Ig can be divided into different subclasses according to the difference in the amino acid composition of the hinge region and the number and position of heavy chain disulfide bonds. For example, IgG can be classified into IgG1, IgG2, IgG3, and IgG4. Light chains can be classified as κ chain or λ chain according to the difference in constant region. Each of the five classes of Ig may have a κ chain or a λ chain.

In this invention, the antibody light chain of this invention can further comprise a light chain constant region, which comprises a human or murine κ, λ, chain or variants thereof.

In this invention, the antibody heavy chain of this invention can further comprise a heavy chain constant region, which comprises a human or murine IgG1, IgG2, IgG3, IgG4 or variants thereof.

Variable region (V region), composed of about 110 amino acids close to the N-terminus of the antibody heavy and light chains, varies considerably in its amino acid sequence. Constant region (C region), composed of the remaining amino acid sequence close to the C-terminus of the antibody, is relatively stable. The variable region comprises three hypervariable regions (HVR) and four relatively conserved framework regions (FR). The three hypervariable regions which determine the specificity of the antibody, are also termed complementarity determining region (CDR). Each of the light chain variable region (VL) and the heavy chain variable region (VH) consists of three CDR regions and four FR regions, arranged from amino terminus to carboxy terminus in the following order: FR1, CDR1, FR2, CDR2, FR3, CDR3 and FR4. The three CDR regions of the light chain refer to LCDR1, LCDR2, and LCDR3; the three CDR regions of the heavy chain refer to HCDR1, HCDR2, and HCDR3. The number and position of CDR amino acid residues of the VL and VH regions of the antibodies or antigen binding fragments of the invention comply with known IMGT numbering criteria.

The term "antigen presenting cell" or "APC" is a cell that displays a foreign antigen complexed with MEW on its surface. T cells recognize this complex through the T cell receptor (TCR). Examples of APCs include, but are not limited to, dendritic cells (DC), peripheral blood mononuclear cells (PBMC), monocytes, B lymphoblasts, and monocyte-derived dendritic cells (DC). The term "antigen presentation" refers to the process by which APCs capture antigens and enable them to be recognized by T cells, for example as a component of MHC-I/MHC-II conjugates.

The term "CD40" refers to cell surface receptor that is a member of the TNF receptor superfamily, also known as TNFRSF5. CD40 is ubiquitously expressed on the surface of dendritic cells, B cells and macrophages and is a molecule required for the production and maintenance of T cell immunity. The term "CD40" includes any variant or isoform of CD40 that is naturally expressed by a cell. The antibodies of the invention can be cross-reactive with CD40 from non-human species. Alternatively, the antibody may be human CD40-specific and may not exhibit cross-reactivity with other species. CD40, or any variant or isoform thereof, can be isolated from cells or tissues in which they are naturally expressed, or produced by recombinant techniques using techniques common in the art and described herein. Preferably, the anti-CD40 antibody targets human CD40 with a normal glycosylation pattern.

The term "recombinant human antibody" includes human antibody that is prepared, expressed, constructed or isolated by recombinant methods, and the techniques and methods involved are well known in the art, such as (1) an antibody isolated from transgenic, transchromosomal animals (e.g., mouse) containing immunoglobulin gene, or hybridomas prepared therefrom; (2) an antibody isolated from host cells transformed to express antibodies, such as a transfectoma; (3) an antibody isolated from a recombinant combinatorial human antibody library, and (4) an antibody prepared, expressed, constructed or isolated by splicing a human immunoglobulin gene sequence to other DNA sequences and the like. Such recombinant human antibody comprises variable regions and constant regions that utilize not only specific human germline immunoglobulin sequences encoded by germline genes, but also subsequent rearrangements and mutations such as those occurring during antibody maturation.

The term "murine antibody" in the present invention is a monoclonal antibody against human CD40 prepared according to the knowledge and skills in the art. The test subject is injected with CD40 antigen at the time of preparation, and then hybridoma expressing the antibody having desired sequence or functional properties is isolated. In a preferable embodiment of the present invention, the murine CD40 antibody or antigen binding fragment thereof may further comprise a light chain constant region of murine κ, λ, chain or variants thereof, or further comprises heavy chain constant region of murine IgG1, IgG2, IgG3 or IgG4 or variants thereof.

The term "human antibody" includes antibodies having variable and constant regions of human germline immunoglobulin sequences. The human antibody of the invention may include amino acid residues not encoded by human germline immunoglobulin sequences (e.g., mutations introduced by random or site-specific mutagenesis in vitro or by somatic mutation in vivo). However, the term "human antibody" does not include an antibody in which CDR sequence derived from the germline of another mammalian species, such as mouse, has been grafted onto human framework sequences (i.e., "humanized antibody").

The term "humanized antibody", also known as CDR-grafted antibody, refers to an antibody produced by grafting a CDR sequence of a murine into the frameworks of a human antibody variable region. It can overcome the intense immune response induced by chimeric antibody carrying a large amount of mouse protein components. To avoid a decrease in activity caused by reducing the immunogenicity, the human antibody variable region can be subjected to minimal reverse mutation to maintain the activity.

The term "chimeric antibody" is an antibody formed by fusing a variable region of a murine antibody with a constant region of a human antibody, which can alleviate the immune response induced by a murine antibody. To construct the chimeric antibody, hybridoma that secretes murine-specific monoclonal antibody is first constructed and selected, then the variable region gene is cloned from the murine hybridoma cell. Subsequently, the constant region gene of the human antibody is cloned as needed. The murine variable region gene and the human constant region gene are ligated into a chimeric gene and then inserted into a human vector, and finally the chimeric antibody molecule is expressed in the eukaryotic or prokaryotic industrial system. The constant region of human antibody may be selected from the heavy chain constant region of human IgG1, IgG2, IgG3 or IgG4 or variants thereof, preferably comprising heavy chain constant region of human IgG1 or IgG2.

The term "antigen binding fragment" refers to an antigen binding fragment of an antibody and an antibody analog, which typically includes at least a portion of an antigen binding region or variable region (e.g., one or more CDRs) of a parental antibody. The antibody fragment retains at least some of the binding specificity of the parent antibody. Generally, the antibody fragment retains at least 10% of the parental binding activity when indicated on a mole basis. Preferably, the antibody fragment retains at least 20%, 50%, 70%, 80%, 90%, 95% or 100% or more of the binding affinity of the parent antibody to the target. Examples of antigen binding fragments include, but are not limited to, Fab, Fab', F(ab')$_2$, Fv fragments, linear antibodies, single chain antibodies, nanobodies, domain antibodies, and multispecific antibodies. Engineered antibody variants are reviewed in Holliger and Hudson (2005) Nat. Biotechnol. 23: 1126-1136.

A "Fab fragment" consists of a light chain, and a CH1 and a variable region of a heavy chain. The heavy chain of a Fab molecule cannot form disulfide bond(s) with another heavy chain molecule.

A "Fc" region contains two heavy chain fragments comprising CH1 and CH2 domains of an antibody. The two heavy chain fragments are held together by two or more disulfide bonds and the hydrophobic interaction of CH3 domains.

A "Fab' fragment" contains a light chain and a portion of a heavy chain comprising a VH domain, a CH1 domain and a region between the CH1 and CH2 domains. Thus, interchain disulfide bonds can be formed between the two heavy chains to form F(ab')$_2$ molecule.

A "F(ab')$_2$ fragment" contains two light chains and two heavy chains containing a portion of the constant region between CH1 and CH2 domains, thereby forming disulfide bonds between the two heavy chains. Thus, the F(ab')$_2$ fragment consists of two Fab' fragments held together by disulfide bonds between two heavy chains.

An "Fv region" contains variable regions from both heavy and light chains, but lacks a constant region.

The term "multi-specific antibody" is used in its broadest sense to encompass antibodies having multi-epitopes specificity. These multi-specific antibodies include, but are not limited to, antibodies comprising a heavy chain variable region (VH) and a light chain variable region (VL), wherein the VH-VL unit has multi-epitopes specificity; antibodies having two or more VL and VH regions, each VH-VL unit binding to a different targets or different epitopes of the same target; antibodies having two or more single variable regions, each single variable region binding to different targets or different epitopes of the same target; full-length antibodies, antibody fragments, diabodies, bispecific diabodies and triabodies, antibody fragments that are covalently or non-covalently linked together and the like.

The term "antibody-drug conjugate" (ADC) refers to an antibody or antibody fragment conjugated to one or more heterologous chemically synthesized molecules, including but not limited to antibody or antibody fragments conjugated to cytotoxic agents.

The term "single-chain antibody" is a single-chain recombinant protein formed by connecting a heavy chain variable region (VH) and a light chain variable region (VL) of an antibody via a linker peptide, which is the smallest antibody fragment with complete antigen binding sites.

The term "domain antibody fragment" is an immunologically functional immunoglobulin fragment containing only a heavy chain variable region or a light chain variable region chain. In some cases, two or more VH regions are covalently linked to a peptide linker to form a bivalent domain antibody fragment. The two VH regions of a bivalent domain antibody fragment can target the same or different antigens.

The term "binding to CD40" as used herein refers to the ability to interact with human CD40. The term "antigen binding site" as used in the present invention refers to a three-dimensional spatial site that is discrete on an antigen and is recognized by an antibody or antigen binding fragment of the present invention.

The term "epitope" refers to a site on an antigen that specifically binds to an immunoglobulin or antibody. An epitope can be formed by adjacent amino acids, non-adjacent amino acid juxtaposed by tertiary folding of a protein. Epitopes formed by adjacent amino acids are typically maintained after exposure to denaturing solvents, while epitopes formed by tertiary folding are typically lost after treatment with denaturing solvents. Epitopes typically include at least 3-15 amino acids in a unique spatial conformation. Methods for determining which epitopes are bound by a given antibody are well known in the art, including immunoblotting and immunoprecipitation assays, and the like. Methods for determining the spatial conformation of epitopes include techniques in the art and techniques described herein, such as X-ray crystallography and two-dimensional nuclear magnetic resonance.

As used herein, the terms "specifically bind" or "selectively bind" refer to the binding of an antibody to an epitope on a predetermined antigen. Typically, when recombinant human CD40 is used as an analyte and an antibody is used as a ligand, the antibody binds to a predetermined antigen with an equilibrium dissociation constant ($K_D$) of less than about $10^{-7}$ M or even less when measured by surface plasmon resonance (SPR) techniques in an instrument, and its affinity for binding to a predetermined antigen is at least twice its affinity for binding to a non-specific antigen (such as BSA, etc.) other than a predetermined antigen or a closely related antigen. The term "antibody(ies) that recognize(s) an antigen" can be used interchangeably herein with the term "antibody(ies) that specifically bind(s)".

The term "cross-reaction" refers to the ability of an antibody of the present invention to bind to CD40 from different species. For example, an antibody of the present invention that binds to human CD40 can also bind to CD40 of another species. Cross-reactivity is measured by detecting specific reactivity of antibodies with purified antigens in binding assays (e.g., SPR and ELISA), or binding or functional interactions of antibodies with cells that express CD40 physiologically. Methods for determining cross-reactivity include standard binding assays, as described herein, such as surface plasmon resonance (SPR) assay, or flow cytometry.

The terms "inhibit", "inhibition", "blockade" or "block" are used interchangeably and encompass both partial and complete inhibition/blockade. The inhibition/blockade of the ligand preferably reduces or alters the normal level or type of activity that occurs when ligand binding arises without inhibition or blockade. Inhibition and blockade are also intended to include any measurable reduction in ligand binding affinity when contacted with an anti-CD40 antibody as compared to a ligand that are not contacted with an anti-CD40 antibody.

The term "inhibition of growth" (e.g., involving cells) is intended to include any measurable reduction in cell growth.

The terms "inducing immune response" and "enhancing immune response" can be used interchangeably and refer to the stimulation (i.e., passive or adaptive) of an immune response to a particular antigen. The term "inducing" specific for inducing CDC or ADCC refers to stimulating specific direct cell killing mechanism.

The "ADCC" described in the present invention, that is, antibody-dependent cell-mediated cytotoxicity, means that cells expressing Fc receptors directly kills target cells coated with antibodies by recognizing Fc segment of the antibody. The ADCC effector function of the antibody can be reduced or eliminated by modification of the Fc segment on IgG. The modification refers to mutations in the heavy chain constant region of the antibody, such as mutations selected from the group consisting of N297A, L234A, L235A of IgG1; IgG2/4 chimera, F235E of IgG4, and L234A/E235A mutation.

Methods for producing and purifying antibodies and antigen binding fragments are well known and can be found in the prior art, such as the Using Antibodies: A Laboratory Manual, Chapters 5-8 and 15, Cold Spring Harbor. For example, a mouse can be immunized with human CD40 or a fragment thereof, and the resulting antibody can be renatured, purified, and subjected to amino acid sequencing by a conventional method. The antigen binding fragment can also be prepared by a conventional method. The antibodies or antigen binding fragments of the present invention are genetically engineered to introduce one or more human FR regions in a non-human CDR region. Human germline FR sequences are available on the website of ImMunoGeneTics (IMGT) http://imgt.cines.fr or from *The Immunoglobulin FactsBook*, 2001 ISBN 014441351.

The engineered antibodies or antigen binding fragments of the present invention can be prepared and purified by conventional methods. The cDNA sequence of the corresponding antibody can be cloned and recombined into a GS expression vector. CHO cells can be stably transfected by the recombinant immunoglobulin expression vector. As a more recommended method well known in the art, mammalian expression systems will result in glycosylation of antibodies, particularly at the highly conserved N-terminus of the FC region. Stable clones are obtained by expressing antibodies that specifically bind to human antigens. Positive clones were expanded in serum-free medium in a bioreactor to produce antibodies. Culture medium, into which the antibody is secreted, can be purified and collected by conventional techniques. The antibody can be concentrated by filtration in a conventional manner. Soluble mixtures and multimers can also be removed by conventional methods such as molecular sieves, ion exchange. The resulting product needs to be frozen immediately, such as −70° C., or lyophilized.

The antibody of the present invention refers to a monoclonal antibody. The monoclonal antibody (mAb) of the present invention refers to an antibody obtained from a single clonal cell line, and the cell line is not limited to a eukaryotic, prokaryotic or phage clonal cell line. Monoclonal antibodies or antigen binding fragments can be obtained recombinantly using, for example, hybridoma technology, recombinant techniques, phage display technology, synthetic techniques (e.g., CDR-grafting), or other prior art techniques.

When applying to an animal, human, experimental subject, cell, tissue, organ or biological fluid, "administration" and "treatment", refer to contacting an exogenous drug, therapeutic agent, diagnostic agent or composition with animal, human, subject, cell, tissue, organ or biological fluid. "Administration" and "treatment" can refer to, for example, therapeutic, pharmacokinetic, diagnostic, research, and experimental methods. Treatment of the cells includes contacting reagents with the cells, as well as contacting reagents with the fluid, wherein the fluids are in contact with the cells. "Administration" and "treatment" also means treating, for example, cells in vitro and ex vivo by reagents, diagnostics, binding compositions, or by another cell. "Treatment", as it applies to a human, veterinary or research subject, refers to therapeutic treatment, prophylactic or preventative measures, to research and diagnostic applications.

"Therapy" means the administration of a therapeutic agent for internal or external use, such as a composition comprising any of the binding compounds of the present invention, to a patient having one or more symptoms of the disease for which the therapeutic agent is known to have therapeutic effect. Generally, the therapeutic agent is administered in an amount that effectively alleviates the symptoms of one or more diseases in a subject or population to be treated, whether by inducing degeneration of such symptoms or inhibiting the progression of such symptoms to any clinically unmeasurable degree. The amount of therapeutic agent (also referred to as "therapeutically effective amount") effective in alleviating the symptoms of any particular disease can vary depending on a variety of factors, such as disease state, age and weight of the patient, and the ability of the drug to elicit a desired effect in the patient. Whether the symptoms of the disease have been alleviated can be assessed by any clinical test method commonly used by a physician or other health care professionals to assess the severity or progression of the condition. Although embodiments of the invention (e.g., therapeutic methods or preparations) may not be effective in ameliorating the symptoms of the target disease common to each patient, it is determined that the symptoms of target disease should be alleviated in a statistically significant number of patients according to any statistical test methods known in the art such as Student's t-test, chi-square test, U test based on Mann and Whitney, Kruskal-Wallis test (H test), Jonckheere-Terpstra test, and Wilcoxon test.

"Conservative modification" or "conservative substitution or replacement" refers to substitution of amino acids in proteins with other amino acid having similar characteristics (e.g., charge, side chain size, hydrophobicity/hydrophilicity, backbone conformation and rigidity, etc.), such that changes can be made frequently without altering the biological activity of the protein. It is known by those skilled in the art that, in general, a single amino acid substitution in a non-essential region of a polypeptide does not substantially alter biological activity (see, for example, Watson et al. (1987) *Molecular Biology of the Gene*, The Benjamin/Cummings Pub. Co., Page 224, (4th edition)). In addition, substitutions of structurally or functionally similar amino acids are unlikely to disrupt biological activity. Common conservative substitutions of amino acids are as follows:

| Original residue | Exemplary substituted residues | Preferable substituted residues |
| --- | --- | --- |
| Ala(A) | Val, leu, ile | val |
| Arg(R) | Lys, gln, asn | lys |
| Asn(N) | Gln, his, asp, lys, arg | gln |
| Asp(D) | Glu, asn | glu |
| Cys(C) | Ser, ala | ser |
| Gln(Q) | Asn, glu | asn |
| Glu(E) | Asp, gln | asp |
| Gly(G) | ala | ala |
| His(H) | Arg, asn, gln, lys | arg |
| Ile(I) | Leu, val, met, ala, phe, Norleucine | leu |
| Leu(L) | Ile, Norleucine, val, met, ala, phe | ile |
| Lys(K) | Arg, gln, asn | arg |
| Met(M) | Leu, phe, ile | leu |
| Phe(F) | Tyr, leu, val, ile, ala | tyr |
| Pro(P) | ala | ala |
| Ser(S) | thr | thr |
| Thr(T) | ser | ser |
| Trp(W) | Tyr, phe | tyr |
| Tyr(Y) | Phe, trp, thr, ser | phe |
| Val(V) | Leu, ile, met, phe, ala, Norleucine | leu |

The term "consisting essentially of" or variations thereof, as used throughout the specification and claims, includes all such elements or groups of elements, and optionally includes other elements that are similar or different in nature to said elements, the other elements do not significantly alter the essential or novel properties of a given dosage regimen, method or composition. As a non-limiting example, a binding compound consisting essentially of the amino acid sequence recited may also include one or more amino acids that do not significantly affect the properties of the binding compound.

The term "naturally occurring" applied to an object according to the present invention refers to the fact that the object can be found in nature. For example, a polypeptide sequence or a polynucleotide sequence that is present in an organism (including viruses) which can be isolated from a natural source and has not been intentionally artificially modified in the laboratory is naturally occurring.

An "effective amount" includes an amount sufficient to ameliorate or prevent a symptom or sign of a medical condition. An effective amount also means an amount sufficient to allow or facilitate the diagnosis. An effective amount for a particular patient or veterinary subject can vary depending on factors such as the condition to be treated, the overall health of the patient, the route and dosage of the method of administration, and the severity of the side effects. An effective amount can be the maximum dose or dosing regimen that avoids significant side effects or toxic effects.

"Exogenous" refers to a substance that is produced outside of a living organism, cell, or human body according to the background. "Endogenous" refers to a substance produced in a cell, organism or human body according to the background.

"Homology" refers to sequence similarity between two polynucleotide or polypeptide sequences. When positions in both comparison sequences are occupied by the same base or amino acid monomer subunit, for example, if each position of two DNA molecules is occupied by adenine, then the molecule is homologous at that position. The percentage of homology between two sequences is a function of the number of matching or homologous positions shared by the two sequences divided by the number of positions compared×100%. For example, when the sequences are optimally aligned, if 6 of 10 positions in the two sequences match or are homologous, then the two sequences are 60% homologous. In general, comparisons are made when the maximum percentage of homology is obtained by aligning the two sequences.

The expressions "cell", "cell line" and "cell culture" as used herein can be used interchangeably and all such names include their progeny. Thus, the words "transformant" and "transformed cells" include primary test cells and cultures derived therefrom, regardless of the number of transfers. It should also be understood that all progeny may not be exactly identical in terms of DNA content due to intentional or unintentional mutations. Mutant progeny having the same function or biological activity as those screened in the originally transformed cell are included. When different names are meant, they are clearly distinguishable from the context.

"Optional" or "optionally" means that the event or environment described subsequently may but does not necessarily occur, including where the event or environment occurs or does not occur. For example, "optionally comprising 1-3 antibody heavy chain variable regions" means that the antibody heavy chain variable region of a particular sequence may, but need not, be present.

"Pharmaceutical composition" means a mixture comprising one or more of the compounds described herein, or a physiologically/pharmaceutically acceptable salt or prodrug thereof, and other chemical components, as well as other components such as physiological/pharmaceutically acceptable carriers and excipients. The purpose of the pharmaceutical composition is to promote the administration of the organism, which facilitates the absorption of the active ingredient and thereby exerts biological activity.

DETAILED DESCRIPTION OF THE PREFERRED EMBODIMENT

The following examples further illustrate the present invention and should not be construed to limit the present invention. Experimental methods without indicating specific conditions in the embodiments of the invention are usually carried out according to conventional conditions, such as Using Antibodies: A Laboratory Manual, or Molecular Cloning: A Laboratory Manual, Cold Spring Harbor Laboratory; or according to the conditions recommended by the manufacturer of raw material or commodity. Reagents without specified source are routine reagents purchased from the market.

EXAMPLE 1 IMMUNE ANTIGEN, SEQUENCE OF SCREENED ANTIGEN AND PREPARATION THEREOF

His-tagged human CD40 (h-CD40-his) recombinant protein, Fc-tagged human CD40 (h-CD40-Fc) recombinant protein, His-tagged mouse CD40 (m-CD40-his) recombinant protein and His-tagged rhesus CD40 (rhesus-CD40-his) recombinant protein (# CD0-052H7) were purified commercial protein purchased from Acrobiosystems, and the sources of their respective sequences are shown in Table 1. These proteins can be used in the experiments of the following examples.

| Name | Start and end of acid sequence | Genbank accession number |
| --- | --- | --- |
| h-CD40-his | Glu21-Arg193 | AAH12419.1 |
| h-CD40-Fc | Glu21-Arg193 | NP_001241.1 |
| m-CD40-his | Val24-Arg193 | P27512 |
| rhesus-CD40-his | Glu21-Arg193 | NP 001252791.1 |

EXAMPLE 2 PREPARATION OF ANTIBODY HYBRIDOMA

Anti-human CD40 monoclonal antibodies were produced by immunizing mice, which are experimental C57BL/6 mice, female, 6-8 weeks old [Zhao Yan (Suzhou) New Drug Research Center Co., Ltd., animal production license number: 201503259]. Feeding environment: SPF level. The mice were purchased and feed in a laboratory environment for 1 week with 12/12 hours light/dark cycle adjustment at a temperature of 20-25° C., and humidity of 40-60%. The mice that have adapted to the environment were divided into 2 cages with 5 mice in each cage.

The immune antigen was an Fc-tagged human modified CD40 recombinant protein (h-CD40-Fc, formulated in phosphate buffer to concentration 1 μg/μl). Freund's adjuvant (Sigma, Lot No.: F5881/F5506) was used for emulsification, wherein, Freund's complete adjuvant (CFA) was used for primary immunization, and nucleic acid adjuvant (CpG, Sangon Biotech) and aluminum for injection (Imject Alum), Thermo, Lot No.: PH203866) for remaining boost immunization. The immunization was performed on Day 0, Day 14, Day 28, Day 42, Day 56, and Day 70. Blood was collected on the 21st, 35th, 49th, 63th, and 77th day for blood test, and the serum of the mouse was detected by ELISA to determine the antibody titer in the serum of the mouse.

Upon fourth immunization, spleen cell fusion was performed in mice, in which the antibody titer is high and tend to stable in serum. Boost immunization was performed 3 days prior to fusion, and 10 μg of antigen solution formulated with phosphate buffer was injected intraperitoneally (IP) in each mouse. The spleen lymphocytes were fused with myeloma cell Sp2/0 cells (ATCC® CRL-8287™) using an optimized PEG-mediated fusion step to obtain hybridoma cells, and five monoclonal hybridoma cell lines with good in vitro activity were selected.

EXAMPLE 3 ELISA BINDING ASSAY

Binding properties of anti-CD40 antibodies was detected by ELISA assay. The CD40 recombinant protein with his-tag was directly used for coating, after the antibody was added, the binding activity of the antibody to the antigen—was detected by adding a secondary antibody (HRP-conjugated anti-antibody Fc antibody) and HRP substrate TMB.

A 96-well microtiter plate was coated with 100 μl/well of human or rhesus CD40-his protein at a concentration of 0.5 μg/ml and incubated overnight at 4° C. The plate was rinsed three times with rinsing buffer, 250 μl per well. For each rinsing, the plate was shaken for 10 seconds to ensure sufficient cleaning. 200 μl blocking solution was added in each well and incubated for 2 hours at room temperature. Then the plate was washed three times with 250 μl per well. The plate was shaken for 10 seconds in each rinsing to ensure sufficient cleaning. 100 μl of anti-CD40 antibody to be tested diluted in dilution was added to each well, and incubated for 1 hour at room temperature, then rinsing the plate for three times with 250 μl of rinsing buffer per well. 100 μl of HRP-labeled goat anti-human IgG secondary antibody diluted 1:20000 with diluent was added to each well, and incubated for 1 hour at room temperature. Then the plate was washed three times with 250 μl per well. 100 μl of TMB was added to each well and allowed to react for 15 minutes in the dark. 50 μl of 0.16 M sulfuric acid per well was added. The OD value was measured at 450 nm by Thermo MpμltiSkanFc plate reader and the binding EC50 value of the CD40 antibody to CD4 was calculated.

TABLE 2

| | ELISA binding of mouse hybridoma antibody to different germline CD40 | | |
| --- | --- | --- | --- |
| Antibody strain | Human CD40-his ELISA EC50 (ng/ml) | Rhesus CD40-his ELISA EC50 (ng/ml) | Mouse CD40-his ELISA EC50 |
| 1D9 | 10.01 | 9.808 | No binding |
| 2H6 | 7.063 | 7.207 | No binding |
| 9E5 | 5.996 | 6.704 | No binding |
| 14C10 | 8.808 | 9.494 | No binding |
| 38B4 | 12.9 | 11.81 | No binding |

EMBODIMENT 4 ANTI-CD40 ANTIBODY BLOCKS THE BINDING OF CD40 AND CD40L

In this experiment, the screened anti-human CD40 antibody is detected to block the binding of human CD40 and human CD40L by an in vitro blocking assay. Specifically, the Fc-tagged CD40 recombinant protein (h-CD40-Fc) was coated onto a 96-well microtiter plate. After anti-CD40 antibody was added to fully bind and occupy epitope, his-tagged CD40L was added. By detecting his tag, the binding amount of CD40 to CD40L was calculated, and then the IC50 value of CD40 antibody blocking CD40 active site was calculated.

A 96-well microtiter plate was coated with 100 μl/well of human or rhesus CD40-Fc protein at a concentration of 1 μg/ml and incubated overnight at 4° C. The plate was rinsed three times with rinsing buffer, 250 μl per well. For each rinsing, the plate was shaken for 10 seconds to ensure sufficient cleaning. 200 μl blocking solution was added in each well and incubated for 2 hours at room temperature. Then the plate was washed three times with 250 μl per well. The plate was shaken for 10 seconds in each rinsing to ensure sufficient cleaning. 100 μl of anti-CD40 antibody to be tested diluted in dilution was added to each well, and incubated for 1 hour at room temperature, then rinsing the plate for three times with 250 μl rinsing buffer per well. 100 μl of HRP-labeled goat anti-human IgG secondary antibody diluted 1:2000 with diluent was added to each well, and incubated for 1 hour at room temperature. Then the plate was washed three times with 250 μl per well. 100 μl of TMB was added to each well and allowed to react for 15 minutes in the dark. 50 μl of 0.16 M sulfuric acid per well was added. The OD value was measured at 450 nm by Thermo MμltiSkanFc plate reader and the IC50 value of CD40 antibody blocking CD40 binding to CD40L was calculated.

TABLE 3

ELISA blocking results of human hCD40/hCD40L

| Antibody strain | ELISA blocking of human hCD40/hCD40L IC50(μg/ml) |
|---|---|
| 1D9 | 0.2634 |
| 2H6 | 0.2682 |
| 9E5 | 0.2787 |
| 14C10 | 0.3001 |
| 38B4 | 0.2934 |

EMBODIMENT 5 BIACORE AFFINITY DETERMINATION

Human antibody captured antibody was covalently coupled to CM5 biosensor chip of Biacore instrument (Biacore X100, GE) according to the method described in the description of Human Antibody Capture Kit (Cat. BR-1008-39, GE), thereby capturing a certain amount of chimeric or humanized antibodies to be tested based on affinity. Then a series of concentration gradient CD40 antigens (purchased from Acrobiosystems) flowed through the surface of chip, and Biacore X100 (GE) was used to detect the reaction signals in real time to obtain the binding and dissociation curves. After the completion of each cycle of dissociation, the biochip was rinsed and regenerated with the regeneration solution provided by the Human Antibody Capture Kit. Amine Coupling Kits (Cat. BR-1000-50, GE) were purchased from GE, and the buffer solution HBS-EP+buffer 1× (pH 7.4), which was obtained from HBS-EP+buffer 10× (Cat. BR-1006-69, GE) by dilution with D. I. Water. The experimental data were fitted by BiacoreX100 Evaluation Software 2.0 (GE software) with a (1:1) Binding model to obtain the affinity values, as shown in tables 10 and 11.

EMBODIMENT 6 CELL ACTIVITY TEST OF ANTI-CD40 ANTIBODY BASED ON REPORTER GENE

HEK-Blue CD40L cells were purchased from Invitrogen (Cat # hkb-cd40), which stably transfected with the human CD40 gene and NF-κB-mediated SEAP genome. Thus, the activation level of the CD40 signaling pathway can be characterized by detecting the secreted SEAP in the supernatant by QUANTI-Blue (the substrate of SEAP). In this experiment, the in vitro cell viability of CD40 antibody was evaluated according to EC50 value by detecting the activation of cellular HEK-Blue CD40L. The HEK-Blue CD40L cells were cultured in DMEM medium containing 10% FBS, 100 μg/ml Zeocin and 30 μg/ml Blasticidin, and passaged 2 to 3 times a week, and the passage ratio was 1:5 or 1:10. When subculturing cells, the medium was removed by pipetting, and the cell layer was rinsed with 5 ml of 0.25% trypsin. Then the trypsin was removed by pipetting, the cells were digested in an incubator for 3 to 5 minutes, followed by suspending cells by fresh medium. 100 μL of cell suspension was added to a 96-well cell culture plate at a density of 5×10^5 cells/ml, and the culture medium was DMEM containing 10% FBS, 100 μg/ml Zeocin and 30 μg/ml Blasticidin. Meanwhile, only 100 μl of sterile water was added to the periphery of the 96-well plate. The plates were incubated in an incubator for 24 hours (37° C., 5% $CO_2$). After the cells adhered to the wall, 100 μl of gradient diluted antibody to be tested was added to each well. The plates were incubated in the incubator for 20-24 hours (37° C., 5% $CO_2$). Then 40 μl of cells supernatant was taken from each well into a new 96-well flat bottom plate, 160 μl of QUANTI-Blue substrate solution was added, and the plate was incubated in the incubator for 1-3 hours in the dark. The absorbance at 620 nm was measured with a microplate reader (Thermo M μlti SkanFc), and the EC50 value was calculated to evaluate the in vitro cell viability of the CD40 antibody.

TABLE 4

Cell Activities of Anti-CD40 antibody based on reporter gene

| Antibody strain | | HEK293-CD40L cells activity assay EC50 (μg/ml) |
|---|---|---|
| 1D9 | + + + | 0.01454 |
| 2H6 | + + + | 0.01511 |
| 9E5 | + + | 0.01712 |
| 14C10 | + + + | 0.01087 |
| 38B4 | + + | 0.0365 |

EMBODIMENT 7 DC CELLS ACTIVATING ASSAY OF ANTI-CD40 ANTIBODY

Figure 2:
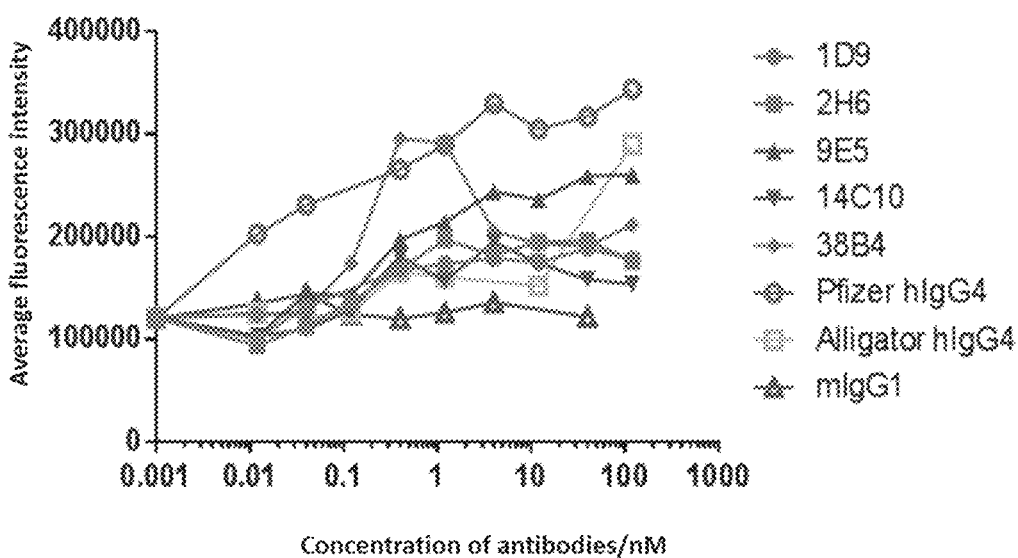
FIG. 2 shows the activation of murine anti-human CD40 antibody on DC cells based on CD86 activating molecules.

PBMCs were isolated from normal human peripheral blood and then monocytes were sorted with CD14 MACS beads. The cells were added with RPMI 1640 medium containing 10 ng/ml IL4 and 100 ng/ml GM-CSF and cultured for 6 days, thereby performing induction culture of MoDC cells (dendritic cells derived from monocytes). After 6 days, the cells were collected, 1×10^5 cells was taken and stained with CD209-PE, CD1a-PerCP/Cy5.5 and CD14-PE/Cy7, and FACS was used to analyze whether the MoDC was induced successfully (the above operations are all conventional operations in the art). Successfully induced DCs were collected, and a variety of antibodies to be tested and reference antibodies with corresponding gradients concentration were added respectively (see FIG. 1 for the gradient concentration of the antibody). Upon 48 hours of culture, cells were harvested and stained with CD80, CD86 and HLA-DR thereafter, and data were collected by FACS assay. According to the data from the primary DC cells activating assay, all the five mouse antibodies showed significant activity and activated the activation molecules CD80 and CD86 on the surface of DCs in a dose-dependent effect. The overall effect of the five antibodies are comparable to or slightly better than that of two reference antibodies (CP-870, 893 of Pfizer and ADC-1013 of Alligator Bioscience). See FIG. 1 and FIG. 2.

EMBODIMENT 8 CLONING AND SEQUENCING OF ANTI-CD40 ANTIBODY

Hybridoma subclones of the five antibodies screened and identified above were selected, and hybridoma cells of which in logarithmic growth phase were collected. RNA was extracted using Trizol (Invitrogen, 15596-018) according to the instruction of kit, and reversely transcribed (PrimeScript™ Reverse Transcriptase, Takara, cat #2680A). Then the resulting cDNA was amplified by PCR using mouse Ig-Primer Set (Novagen, TB326 Rev. B 0503), and sent to sequencing company for sequencing. The sequences of 5 mouse antibodies were finally obtained.

The heavy and light chain variable region sequences of mouse mAb 2H6 are as follows:

2H6 HCVR
SEQ ID NO: 1
QVQLQQSGAELVRPGTSVKVSCKASGYAFSDYLIEWAKQRPGQGLEWIGV
INPGSGGSNYNEKIKDRATLTADKSSTAYMQLSSLTSEDSAVYFCARGG
GGFTYWGQGTLVTVSA

2H6 LCVR
SEQ ID NO: 2
EIQLTQTTSSLSASLGDRVTISCRASQDISNYLNWYQQKPDGTIKLLLNF
ASRLHSGVPSRFSGSGSGTDFFLTISNLEQDDIATYFCQQGSTLPWTFGG
GTKLEIK

CDR sequences of mAb 2H6 are shown in Table 5 below:

TABLE 5

| Name | Sequence | Number |
|---|---|---|
| HCDR1 | GYAFSDYLIE | SEQ ID NO: 3 |
| HCDR2 | VINPGSGGSNYNEKIKD | SEQ ID NO: 4 |
| HCDR3 | GGGGFTY | SEQ ID NO: 5 |
| LCDR1 | RASQDISNYLN | SEQ ID NO: 6 |
| LCDR2 | FASRLHS | SEQ ID NO: 7 |
| LCDR3 | QQGSTLPWT | SEQ ID NO: 8 |

The heavy and light chain variable region sequences of mouse 9E5 are as follows:

9E5 HCVR
SEQ ID NO: 9
QVQLQQPGADLVKPGASVKMSCKASGYILTTYWITWVKQRPGQGLEWIGD
IHPGSGSTKYNEKFKSKATLTVDTSSSTAYMQLTRLSSEDSAVYYCARRD
YWGQGTTLTVSS

9E5 LCVR
SEQ ID NO: 10
DVLMTQSPLSLPVSLGDQASISCRSSQNIVNSQGNTYLEWYLQKPGESPK
LLIYKVTNRFSGVPDRFSGSGSGTDFTLKISRVEAEDLGVYYCFQASLVP
WTFGGGTKLEIK

CDR sequences of 9E5 are shown in Table 6 below:

TABLE 6

| Name | Sequence | Number |
|---|---|---|
| HCDR1 | GYILTTYWIT | SEQ ID NO: 11 |
| HCDR2 | DIHPGSGSTKYNEKFKS | SEQ ID NO: 12 |

TABLE 6-continued

| Name | Sequence | Number |
|---|---|---|
| HCDR3 | RDY | SEQ ID NO: 13 |
| LCDR1 | RSSQNIVNSQGNTYLE | SEQ ID NO: 14 |
| LCDR2 | KVTNRFS | SEQ ID NO: 15 |
| LCDR3 | FQASLVPWT | SEQ ID NO: 16 |

The heavy and light chain variable region sequences of 1D9 are as follows:

1D9 HCVR
SEQ ID NO: 37
QVRLQQSGAELVRPGTSMRVSCKASGYAFTNYLINWVKQRPGQGLEWIGI
LNPGSGGTNYNENFKDKATLTADKSSNTAYMQLSSLTSEDSAVYFCIRGS
PGFAYWGQGTLVTVSA

1D9 LCVR
SEQ ID NO: 38
DIQMTQTTSSLSASLGDRVTISCRASQDINIYLNWYQQKPDGTVKLLIYS
TSGLHSGVPSRFNGSGSGTDYSLTISNLEQEDIATYFCQQGYTLPYTFGG
GTKLEIK

CDR sequences of 1D9 are shown in Table 7 below:

TABLE 7

| Name | Sequence | Number |
|---|---|---|
| HCDR1 | GYAFTNYLIN | SEQ ID NO: 39 |
| HCDR2 | ILNPGSGGTNYNENFKD | SEQ ID NO: 40 |
| HCDR3 | GSPGFAY | SEQ ID NO: 41 |
| LCDR1 | RASQDINIYLN | SEQ ID NO: 42 |
| LCDR2 | STSGLHS | SEQ ID NO: 43 |
| LCDR3 | QQGYTLPYT | SEQ ID NO: 44 |

The heavy and light chain variable region sequences of 14C10 are as follows:

14C10 HCVR
SEQ ID NO: 45
QVQVQQSGAELVRPGTSVKVSCKASGYAFTNYLIEWVKQRPGQGLEWIGV
INPEFGGTNYNEKFKGKATLTADKSSSTAYMQLSSLTSEDSAVYFCARGG
GGFTYWGQGTLVTVSA

14C10 LC VR
SEQ ID NO: 46
HIQMTQTTSSLSASLGDRVTISCRASQDISSHLNWYQQKPDGTVKLLISY
TSRLHSGVPSRFSGSGSGADYSLTISNLEQEDIATYFCQQGNTLPWTFGG
GTKLEIK

CDR sequences of 14C10 are shown in Table 8 below:

TABLE 8

| Name | Sequence | Number |
|---|---|---|
| HCDR1 | GYAFTNYLIE | SEQID NO: 47 |
| HCDR2 | VINPEFGGTNYNEKFKG | SEQID NO: 48 |
| HCDR3 | GGGGFTY | SEQID NO: 49 |
| LCDR1 | RASQDISSHLN | SEQID NO: 50 |
| LCDR2 | YTSRLHS | SEQID NO: 51 |
| LCDR3 | QQGNTLPWT | SEQID NO: 52 |

The heavy and light chain variable region sequences of 38B4 are as follows:

38B4 HCVR

SEQ ID NO: 53
QVRLKQSGAELVRPGASVKVSCKASGYTFTDYYINWVKQRPGQGLEWIAG

IYPGTGNTYYNEKFKGKATLTAERSSSTAYMQLTSLTSEDSAVYFCTRRG

LPSLCFDYWGQGTTLTVSS

38B4 LCVR

SEQ ID NO: 54
DFQMTQTTSSLSASLGDRVTISCSASQGISNYLNWYQQKPDGTVKLLIYY

TSSLHSGVPSRFSGSGSGTDYSLTISNLEPEDIATYYCQQYSKLPPTFGG

GTKLEIK

CDR sequences of 38B4 are shown in Table 9 below:

TABLE 9

| Name | Sequence | Number |
|---|---|---|
| HCDR1 | GYTFTDYYIN | SEQID NO: 55 |
| HCDR2 | GIYPGTGNTYYNEKFKG | SEQID NO: 56 |
| HCDR3 | RGLPSLCFDY | SEQID NO: 57 |
| LCDR1 | SASQGISNYLN | SEQID NO: 58 |
| LCDR2 | YTSSLHS | SEQID NO: 59 |
| LCDR3 | QQYSKLPPT | SEQID NO: 60 |

Among them, two optimal antibodies 2H6 and 9E5 were subjected to the subsequent development. The obtained variable region sequences were ligated to the constant region sequence of human antibody IgG1 respectively to obtain a human-mouse chimeric antibody sequence, and the sequence of the chimeric antibody was inserted into the pCP expression vector (purchased from MabSpace biology Co., Ltd) by molecular cloning technique. These sequences were sequenced and identified after amplifying by PCR (the molecular biological operation methods such as molecular cloning are carried out according to the conventional operating conditions, and can be referred to the "Molecular Cloning: A Laboratory Manual" specifically), and the HEK293 cell expression system can be used to obtain human-mouse chimeric antibodies 2H6-C and 9E5-C. Various in vitro activity assays were performed to characterize chimeric antibodies purified by Mab Select SuRe (GE Lifesciences) affinity chromatography. The data are shown in Table 10.

TABLE 10

In vitro activity of chimeric antibodies

| Chimeric antibody | Human CD40-his ELISA EC50 (ng/ml) | Human hCD40/hCD40L ELISA blocking IC50 (μg/ml) | HEK293-CD40 cells binding EC50 (μg/ml) | Biacore Affinity $K_D$ (nM) |
|---|---|---|---|---|
| 2H6-C | 4.565 | 0.6275 | 0.02593 | 3.98 |
| 9E5-C | 1.346 | 0.1218 | 0.03333 | 2.68 |
| Pfizer reference (hIgG4) | 5.628 | 0.2583 | 0.01638 | 20.35 |
| Alligator reference (hIgG1) | 3.288 | 0.7233 | 0.39650 | 65.9 |

EMBODIMENT 9 MURINE ANTIBODY HUMANIZATION EXPERIMENT

Based on the typical VH/VLCDR structure of the mouse antibodies 2H6 and 9E5 obtained, the heavy and light chain variable region sequences were compared with the antibody Germline database to obtain a human germline template with high homology. Wherein the human germline light chain framework region is derived from a human κ light chain gene, and the light chain framework region of the antibody of the present invention is preferably a human germline light chain template Vk1-33/JK4 (2H6) or Vk2-28/JK4 (9E5). The human germline heavy chain framework region is derived from a human heavy chain, and the heavy chain framework region of the antibody of the present invention is preferably a human germline heavy chain template VH1-69/JH6 (2H6) or VH1-2/JH6 (9E5), as shown below:

The heavy chain framework region of 2H6 is preferably a human germline heavy chain template IGHV1-69 (SEQ ID NO: 21):
QVQLVQSGAEVKKPGSSVKVSCKASGGTFSSYAISWVRQAPGQGLEWMGG

IIPIFGTANYAQKFQGRVTITADKSTSTAYMELSSLRSEDTAVYYCAR

The light chain framework region of 2H6 is preferably a human germline light chain template IGkV1-33(SEQ ID NO: 22):
DIQMTQSPSSLSASVGDRVTITCQASQDISNYLNWYQQKPGKAPKLLIYD

ASNLETGVPSRFSGSGSGTDFTFTISSLQPEDIATYYCQQYDNLP

The heavy chain framework region of 9E5 is preferably a human germline heavy chain template IGHV1-2 (SEQ ID NO: 23):
QVQLVQSGAEVKKPGASVKVSCKASGYTFTGYYMHWVRQAPGQGLEWMG

WINPNSGGTNYAQKFQGRVTMTRDTSISTAYMELSRLSDDTAVYYCAR

The light chain framework region of 9E5 is preferably a human germline light chain template IGkV2-28 (SEQ ID NO: 24):
DIVMTQSPL SLPVTPGEPASISCRSSQSLLHSNGYNYLDWYLQKPGQSP

QLLIYLGSNRASGVPDRFSGSGSGTDFTLKISRVEAEDVGVYYCMQALQT

P

The CDR regions of the murine antibody were grafted onto the selected humanized template to replace the humanized variable region, and then recombined with the corresponding human IgG constant region (preferably the heavy chain is IgG1 and the light chain is κ). Then, based on the three-dimensional structure of the murine antibody, the embedded residues, the residues which have an direct interaction with the CDRs and the residues which have an important influence on the conformation of VL and VH, are subjected to reverse mutation, and the chemically labile amino acid residues of CDR regions are optimized to obtain the final humanized molecule. Heavy chain variable region sequences thereof are set forth in SEQ ID NOS: 25-30, and the light chain variable region sequences are set forth in SEQ ID NOs: 31-36.

```
hu2H6-H1a (SEQ ID NO: 25):
QVQLVQSGAEVKKPGSSVKVSCKASGGTFSDYLIEWVRQAPGQGLEWMGV

INPGSGGSNYNEKIKDRVTITADKSTSTAYMELSSLRSEDTAVYYCARGG

GGFTYWGQGTLVTVSS hu2H6-H1b (SEQ ID NO: 26):
QVQLVQSGAEVKKPGSSVKVSCKASGYAFSDYLIEWVRQAPGQGLEWMGV

INPGSGGSNYNEKIKDRVTLTADKSTSTAYMELSSLRSEDTAVYYCARGG

GGFTYWGQGTLVTVSS hu2H6-H1c (SEQ ID NO: 27):
QVQLVQSGAEVKKPGSSVKVSCKASGYAFSDYLIEWVRQAPGQGLEWIGV

INPGSGGSNYNEKIKDRATLTADKSTSTAYMELSSLRSEDTAVYYCARGG

GGFTYWGQGTLVTVSSFGQGTKLEIK hu9E5-H1a (SEQ ID NO: 28):
QVQLVQSGAEVKKPGASVKVSCKASGYTFTTYWITWVRQAPGQGLEWMGD

IHPGSGSTKYNEKFKSRVTMTVDTSISTAYMELSRLRSEDTAVYYCARRD

YWGQGTTVTVSS hu9E5-H1b (SEQ ID NO: 29):
QVQLVQSGAEVKKPGASVKVSCKASGYTFTTYWITWVRQAPGQGLEWMGD

IHPGSGSTKYNEKFKSRVTLTVDTSISTAYMELSRLRSEDTAVYYCARRD

YWGQGTTVTVSS hu9E5-H1c (SEQ ID NO: 30):
QVQLVQSGAEVKKPGASVKVSCKASGYILTTYWITWVRQAPGQGLEWMGD

IHPGSGSTKYNEKFKSRVTLTVDTSISTAYMELSRLRSEDTAVYYCARRD

YWGQGTTVTVSS hu2H6-L1a (SEQ ID NO: 31):
DIQMTQSPSSLSASVGDRVTITCRASQDISNYLNWYQQKPGKAPKLLLNF

ASRLHSGVPSRFSGSGSGTDFTFTISSLQPEDIATYYCQQGSTLPWTFGG

GTKVEIK hu2H6-L1b (SEQ ID NO: 32):
DIQLTQSPSSLSASVGDRVTITCRASQDISNYLNWYQQKPGKAPKLLLNF

ASRLHSGVPSRFSGSGSGTDFTFTISSLQPEDIATYYCQQGSTLPWTFGG

GTKVEIK hu2H6-L1c (SEQ ID NO: 33):
DIQLTQSPSSLSASVGDRVTITCRASQDISNYLNWYQQKPGKTIKLLLNF

ASRLHSGVPSRFSGSGSGTDFTFTISSLQPEDIATYYCQQGSTLPWTFGG

GTKVEIK hu9E5-L1a (SEQ ID NO: 34):
DIVMTQSPLSLPVTPGEPASISCRSSQNIVNSQGNTYLEWYLQKPGQSPQ

LLIYKVTNRFSGVPDRFSGSGSGTDFTLKISRVEAEDVGVYYCFQASLVP

WTFGGGTKVEIK hu9E5-L1b (SEQ ID NO: 35):
DVVMTQSPLSLPVTPGEPASISCRSSQNIVNSQGNTYLEWYLQKPGQSPQ

LLIYKVTNRFSGVPDRFSGSGSGTDFTLKISRVEAEDVGVYYCFQASLVPW

TFGGGTKVEIK hu9E5-L1c (SEQ ID NO: 36):
DVLMTQSPLSLPVTPGEPASISCRSSQNIVNSQGNTYLEWYLQKPGQSPQ

LLIYKVTNRFSGVPDRFSGSGSGTDFTLKISRVEAEDVGVYYCFQASLVP

WTFGGGTKVEIK
```

The final humanized hu2H6 (comprising H1b heavy chain and L1c light chain) and the hu9E5 antibody molecule (comprising H1c heavy chain and L1a light chain) were selected via the above expression tests and comparison of the number of reverse mutations of the light and heavy chain combinations, and the complete light and heavy chain sequences of which are set forth in SEQ ID NOs: 17-20, respectively.

```
hu2H6 HC
                                        SEQ ID NO: 17
QVQLVQSGAEVKKPGSSVKVSCKASGYAFSDYLIEWVRQAPGQGLEWMGV

INPGSGGSNYNEKIKDRVTLTADKSTSTAYMELSSLRSEDTAVYYCARGG

GGFTYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK hu2H6 LC
                                        SEQ ID NO: 18
DIQLTQSPSSLSASVGDRVTITCRASQDISNYLNWYQQKPGKTIKLLLNF

ASRLHSGVPSRFSGSGSGTDFTFTISSLQPEDIATYYCQQGSTLPWTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC hu9E5 HC
                                        SEQ ID NO: 19
QVQLVQSGAEVKKPGASVKVSCKASGYILTTYWITWVRQAPGQGLEWMGD

IHPGSGSTKYNEKFKSRVTLTVDTSISTAYMELSRLRSEDTAVYYCARRD

YWGQGTTVTVSSASTKGPSVFPLAPSSKSTSGGTAALGCLVKDYFPEPVT

VSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPGK hu9E5 LC
```

-continued

SEQ ID NO: 20

DIVMTQSPLSLPVTPGEPASISCRSSQNIVNSQGNTYLEWYLQKPGQSPQ

LLIYKVTNRFSGVPDRFSGSGSGTDFTLKISRVEAEDVGVYYCFQASLVP

WTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

EMBODIMENT 10 HUMANIZED ANTIBODY TEST DATA

The binding activity, blocking activity, and the like of the humanized antibodies hu2H6 and hu9E5 of the present invention to human, rhesus CD40 are shown in Table 11. The results showed that the ELISA binding and blocking activity of the humanized anti-human CD40 antibody of the present invention was comparable to that of the positive antibody pfizer/alligator. In particular, the Biacore measurement affinity of hu9E5 to human CD40 was 9 times more than that of the positive antibody Alligator reference, and 3 times more than that of the Pfizer reference.

TABLE 11

In vitro activity of humanized hu2H6 and hu9E5 antibodies

|  | Human CD40-his ELISA EC50 (ng/ml) | Rhesus CD40-his ELISA EC50 (ng/ml) | Human hCD40/hCD40L ELISA blocking IC50 (µg/ml) | HEK293-CD40cells binding EC50 (µg/ml) | Biacore affinity $K_D$ (M) |
|---|---|---|---|---|---|
| Hu2H6-11 | 3.680 | 2.945 | 0.6735 | 0.01538 | 1.120E-8 |
| Hu9E5-25 | 1.650 | 1.661 | 0.3084 | 0.13970 | 5.301E-9 |
| Alligator reference (hIgG1) | 1.293 | 1.243 | 0.6471 | 1.36200 | 1.66E-7 |
| Pfizer reference (hIgG4) | 3.976 | 3.561 | 0.3106 | 0.01907 | 2.035E-8 |

EMBODIMENT 11 INHIBITION OF ANTI-CD40 ANTIBODY ON TUMOR GROWTH IN MICE

The normal human peripheral blood was taken and the healthy human PBMC was isolated by density gradient centrifugation. Monocytes were sorted using the CD14+ microbeads kit, and CD14+ monocytes were isolated according to the protocol provided with the kit, ie, 20 µl of Anti-CD14 microbeads were added for each $10^7$ cells, and incubated at 4° C. for 15 minutes. Then, the cells were added to a magnetic column, and rinsed for three times. Cells in the magnetic column, that is, CD14+ monocytes were collected. The RPMI 1640 medium containing 10 ng/ml IL4 and 100 ng/ml GM-CSF was added to the CD14+ monocytes, thereby culturing the monocytes for 6 days (culture method is a common method in the art) to perform induction culture of MoDC cells. RPMI 1640 containing IL-2 was added to the remaining cells, and the suspended cells were collected after culturing (the culture method and the method of collecting the cells are all conventional methods in the art). T cells were sorted using the CD3+ microbeads kit. Six days later, MoDC cells and CD3+ T cells were collected and mixed with Raji cells (Shanghai Institute of Biotechnology Cell Bank, cultured in RPMI1640 medium containing 10% fetal bovine serum) at a ratio of 1:5:20, respectively, and inoculated into each NOG mouse (Nanjing Galaxy Biopharma, adaptive feeding for 5 days) subcutaneously. The experimental animals were kept in an independent ventilated box with constant temperature and humidity. The temperature of the breeding room was 18.0-26.0° C., the humidity was 40-70%, the ventilation was performed for 10-20 times/hour, and the day and night was switched by 12 h/12 h.

The experimental groups include human IgG1 antibody control group, hu2H6, hu9E5 and reference antibody G12, and the dose for each group was 3 mg/kg. Five mice in each group were administered once a week for six weeks with three consecutive administrations. During the whole experiment, the long-axis diameter and the broad-axis diameter of the tumor were measured twice a week using a vernier caliper, and the tumor volume $(mm^3)$=0.5×(tumor long-axis diameter×tumor broad-axis diameter$^2$) was calculated. Relative tumor inhibition rate TGI (%): TGI %=(1−T/C)×100%. T/C % is the relative tumor growth rate, that is, the percentage of relative tumor volume or tumor weight of the treatment group and the control group at a certain time point. T and C are the tumor volume (TV) or tumor weight (TW) of the treatment group and the IgG1 control group at a specific time point, respectively.

Figure 3:
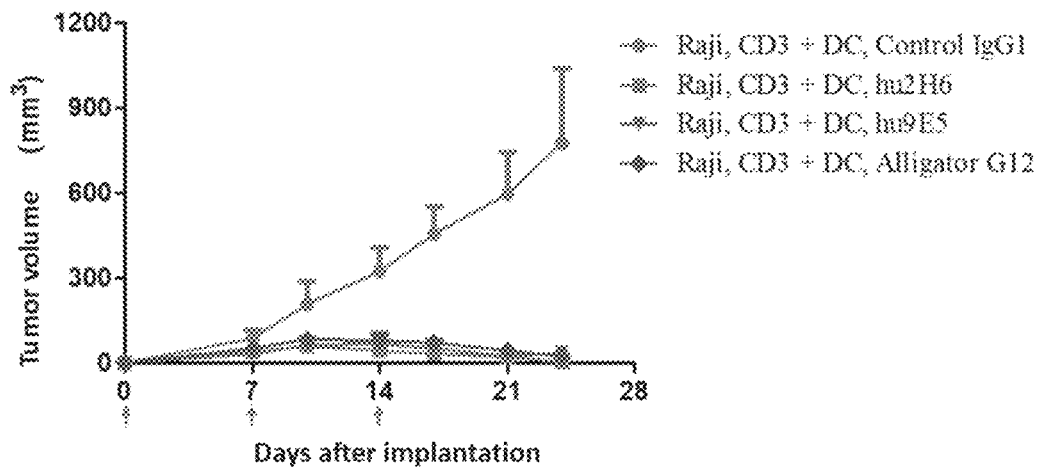
FIG. 3 is a graph showing tumor growth curves of Raji transplanted lymphoma co-transplanted with human PBMC and DC cells.
Figure 4:
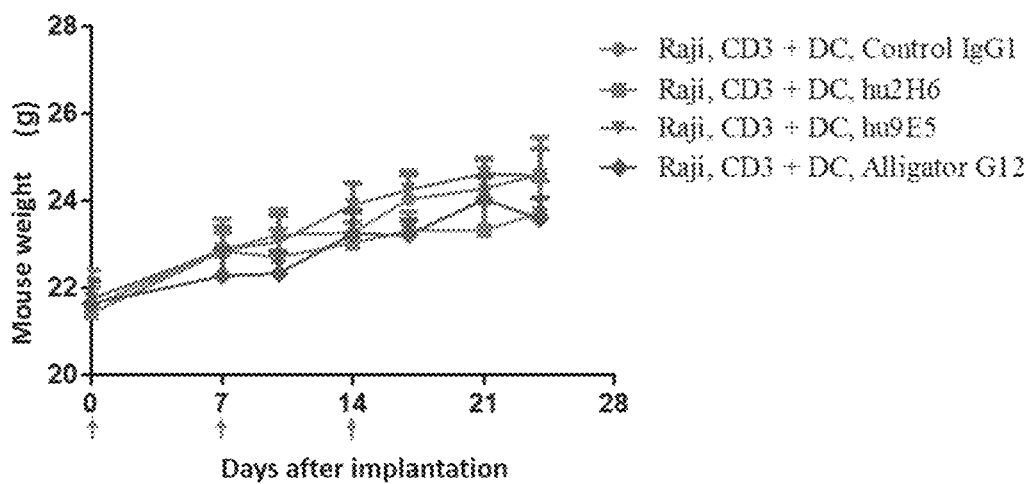
FIG. 4 is a graph showing body weight changes of NOG mice transplanted with Raji-transplanted lymphoma co-transplanted with human PBMC and DC cells.

The results showed that the humanized anti-CD40 antibodies hu2H6 and hu9E5 had very significant anti-tumor effect compared to IgG1 control, and the tumor was almost completely eliminated after 21 days of administration; the anti-tumor effect of hu2H6 and hu9E5 were generally equivalent to, or slightly better than, the reference antibody G12, as shown in the FIG. 3 and FIG. 4.

Although specific embodiments of the present invention have been described above, those skilled in the art should understand that these are merely illustrative, and various changes or modifications can be made to the present invention without departing from the principles and spirits of the present invention, and these equivalent forms also fall within the scope defined by the appended claims of the present application.

What is claimed is:

1. An anti-CD40 antibody or antigen binding fragment thereof, comprising a light chain variable region and a heavy chain variable region, wherein the light chain variable region of the antibody or antigen binding fragment thereof comprises LCDR1, LCDR2 and LCDR3 having the sequence of SEQ ID NO: 6, SEQ ID NO: 7 and SEQ ID NO: 8, respectively; and the heavy chain variable region of the antibody or antigen binding fragment thereof comprises HCDR1, HCDR2 and HCDR3 having the sequence of SEQ ID NO: 3, SEQ ID NO: 4 and SEQ ID NO: 5, respectively; the light chain variable region of the antibody or antigen binding fragment thereof comprises LCDR1, LCDR2 and LCDR3 having the sequence of SEQ ID NO: 14, SEQ ID NO: 15 and SEQ ID NO: 16, respectively; and the heavy chain variable region of the antibody or antigen binding fragment thereof comprises HCDR1, HCDR2 and HCDR3 having the sequence of SEQ ID NO: 11, SEQ ID NO: 12 and SEQ ID NO: 13, respectively; the light chain variable region of the antibody or antigen binding fragment thereof comprises LCDR1, LCDR2 and LCDR3 having the sequence of SEQ ID NO: 42, SEQ ID NO: 43 and SEQ ID NO: 44, respectively; and the heavy chain variable region of the antibody or antigen binding fragment thereof comprises HCDR1, HCDR2 and HCDR3 having the sequence of SEQ ID NO: 39, SEQ ID NO: 40 and SEQ ID NO: 41, respectively; the light chain variable region of the antibody or antigen binding fragment thereof comprises LCDR1, LCDR2, and LCDR3 having the sequence of SEQ ID NO: 50, SEQ ID NO: 51, and SEQ ID NO: 52, respectively; and the heavy chain variable region of the antibody or antigen binding fragment thereof comprises HCDR1, HCDR2, and HCDR3 having the sequence of SEQ ID NO: 47, SEQ ID NO: 48, and SEQ ID NO: 49, respectively; or the light chain variable region of the antibody or antigen binding fragment thereof comprises LCDR1, LCDR2, and LCDR3 having the sequence of SEQ ID NO: 58, SEQ ID NO: 59, and SEQ ID NO: 60, respectively; and the heavy chain variable region of the antibody or antigen binding fragment thereof comprises HCDR1, HCDR2, and HCDR3 having the sequence of SEQ ID NO: 55, SEQ ID NO: 56, and SEQ ID NO: 57, respectively.

2. The anti-CD40 antibody or antigen binding fragment thereof of claim 1, wherein the antibody or antigen binding fragment thereof is a murine antibody or a chimeric antibody.

3. The anti-CD40 antibody or antigen binding fragment thereof of claim 2, wherein the heavy chain variable region comprises SEQ ID NO: 1, and the light chain variable region comprises SEQ ID NO. 2.

4. The anti-CD40 antibody or antigen binding fragment thereof of claim 1, wherein the antibody or antigen binding fragment thereof is a humanized antibody or humanized antigen binding fragment thereof, or a human antibody or human antigen binding fragment thereof.

5. The anti-CD40 antibody or antigen binding fragment thereof of claim 4, wherein the sequence of light chain framework region (FR) on the light chain variable region of the humanized antibody or humanized antigen binding fragment thereof is derived from light chain IGkV1-33 sequence of human germline as shown in SEQ ID NO: 22, or light chain IGkV2-28 sequence of human germline as shown in SEQ ID NO: 24.

6. The anti-CD40 antibody or antigen binding fragment thereof of claim 4, wherein the antibody or antigen binding fragment thereof comprises a light chain sequence of SEQ ID NO: 18 or SEQ ID NO: 20.

7. The anti-CD40 antibody or antigen binding fragment thereof of claim 4, wherein the antibody or antigen binding fragment thereof comprises human IgG1, IgG2, IgG3 or IgG4 constant regions.

8. The anti-CD40 antibody or antigen binding fragment thereof of claim 4, wherein the sequence of heavy chain FR region on the heavy chain variable region of the humanized antibody or humanized antigen binding fragment thereof is derived from heavy chain IGHV1-69 sequence of human germline as shown in SEQ ID NO: 21, or heavy chain IGHV1-2 sequence of human germline as shown in SEQ ID NO: 23.

9. The anti-CD40 antibody or antigen binding fragment thereof of claim 4, wherein the antibody or antigen binding fragment thereof comprises a heavy chain sequence of SEQ ID NO: 17 or SEQ ID NO: 19.

10. The anti-CD40 antibody or antigen binding fragment thereof of claim 1, wherein the heavy chain variable region comprises SEQ ID NO: 26, and the light chain variable region comprises SEQ ID NO: 33.

11. The anti-CD40 antibody or antigen binding fragment thereof of claim 1, wherein the antibody or antigen binding fragment thereof comprise a heavy chain sequence of SEQ ID NO: 19, and a light chain sequence of SEQ ID NO: 20.

12. The anti-CD40 antibody or antigen binding fragment thereof of claim 1, wherein the antibody or antigen binding fragment thereof is a multi-specific antibody.

13. The anti-CD40 antibody or antigen binding fragment thereof of claim 1, wherein the antibody or antigen binding fragment thereof is a single chain antibody.

14. An antibody-drug conjugate, wherein the antibody-drug conjugate comprises the anti-CD40 antibody or antigen binding fragment thereof of claim 1.

15. A pharmaceutical composition comprising the anti-CD40 antibody or antigen binding fragment thereof of claim 1, and a pharmaceutically acceptable excipient, diluent or carrier.

16. A method for treating lymphoma, the method comprises administering to a subject a therapeutically effective dose of the pharmaceutical composition of claim 15.

17. The anti-CD40 antibody or antigen binding fragment thereof of claim 1, wherein the light chain variable region comprises LCDR1, LCDR2 and LCDR3 having the sequence of SEQ ID NO: 6, SEQ ID NO: 7 and SEQ ID NO: 8, respectively; and the heavy chain variable region comprises HCDR1, HCDR2 and HCDR3 having the sequence of SEQ ID NO: 3, SEQ ID NO: 4 and SEQ ID NO: 5, respectively.

18. The anti-CD40 antibody or antigen binding fragment thereof of claim 1, wherein the light chain variable region comprises LCDR1, LCDR2 and LCDR3 having the sequence of SEQ ID NO: 14, SEQ ID NO: 15 and SEQ ID NO: 16, respectively; and the heavy chain variable region comprises HCDR1, HCDR2 and HCDR3 having the sequence of SEQ ID NO: 11, SEQ ID NO: 12 and SEQ ID NO: 13, respectively.

19. The anti-CD40 antibody or antigen binding fragment thereof of claim 1, wherein the heavy chain variable region comprise SEQ ID NO: 30, and the light chain variable region comprise SEQ ID NO: 34.

20. The anti-CD40 antibody or antigen binding fragment thereof of claim 1, wherein the antibody or antigen binding fragment thereof comprise a heavy chain sequence of SEQ ID NO: 17, and a light chain sequence of SEQ ID NO: 18.

21. The anti-CD40 antibody or antigen binding fragment thereof of claim 1, wherein the light chain variable region comprises LCDR1, LCDR2 and LCDR3 having the sequence of SEQ ID NO: 42, SEQ ID NO: 43 and SEQ ID NO: 44, respectively; and the heavy chain variable region comprises HCDR1, HCDR2 and HCDR3 having the sequence of SEQ ID NO: 39, SEQ ID NO: 40 and SEQ ID NO: 41, respectively.

22. The anti-CD40 antibody or antigen binding fragment thereof of claim 1, wherein the light chain variable region comprises LCDR1, LCDR2 and LCDR3 having the sequence of SEQ ID NO: 50, SEQ ID NO: 51 and SEQ ID NO: 52, respectively; and the heavy chain variable region comprises HCDR1, HCDR2 and HCDR3 having the sequence of SEQ ID NO: 47, SEQ ID NO: 48 and SEQ ID NO: 49, respectively.

23. The anti-CD40 antibody or antigen binding fragment thereof of claim 1, wherein the light chain variable region comprises LCDR1, LCDR2 and LCDR3 having the sequence of SEQ ID NO: 58, SEQ ID NO: 59 and SEQ ID NO: 60, respectively; and the heavy chain variable region comprises HCDR1, HCDR2 and HCDR3 having the sequence of SEQ ID NO: 55, SEQ ID NO: 56 and SEQ ID NO: 57, respectively.

24. An anti-CD40 antibody or antigen-binding fragment thereof, wherein HCDR1, HCDR2, and HCDR3 of the antibody or antigen-binding fragment thereof are 100% identical to complementarity determining regions of SEQ ID NO: 30 and LCDR1, LCDR2, and LCDR3 of the antibody or antigen-binding fragment thereof are 100% identical to complementarity determining regions of SEQ ID NO: 34.

25. An anti-CD40 antibody or antigen-binding fragment thereof, wherein HCDR1, HCDR2, and HCDR3 of the antibody or antigen-binding fragment thereof are 100% identical to complementarity determining regions of SEQ ID NO: 26 and LCDR1, LCDR2, and LCDR3 of the antibody or antigen-binding fragment thereof are 100% identical to complementarity determining regions of SEQ ID NO: 33.

* * * * *